Figure 1:
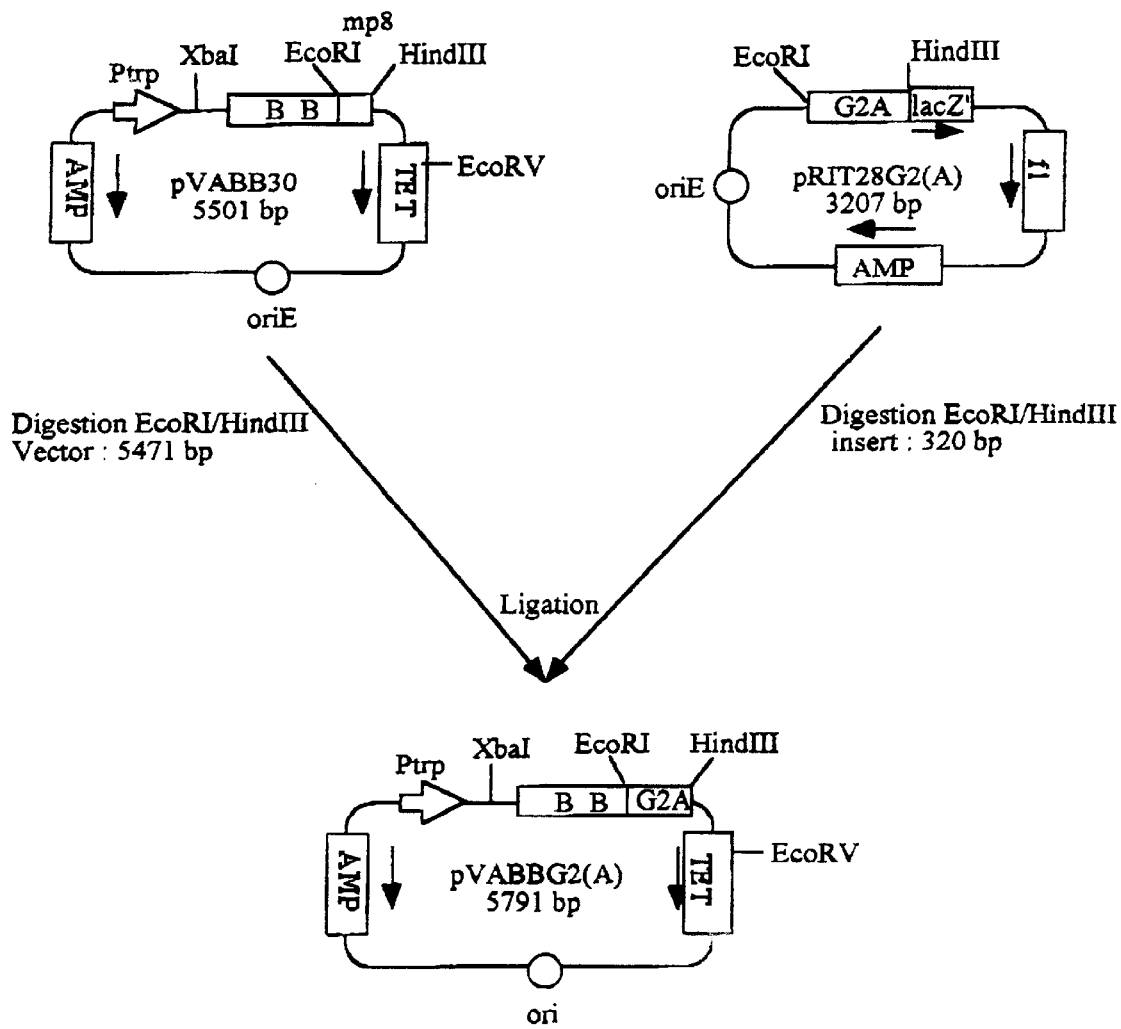

United States Patent [19]
Binz et al.

[11] Patent Number: 6,149,911
[45] Date of Patent: Nov. 21, 2000

[54] METHOD FOR ENHANCING THE IMMUNOGENICITY OF AN IMMUNOGENIC COMPOUND OR HAPTEN, AND USE THEREOF FOR PREPARING VACCINES

[75] Inventors: Hans Binz, Beaumont; Thien Nguyen Ngoc, St. Julien en Genevois; Christine Andreoni, Nantua, all of France; Per Ake Nygren, Skarpnack, Sweden; Stefan Stahl; Mathias Uhlen, both of Stockholm, Sweden

[73] Assignee: Pierre Fabre Medicament, Boulogne, France

[21] Appl. No.: 08/836,501

[22] PCT Filed: Nov. 7, 1995

[86] PCT No.: PCT/FR95/01466

§ 371 Date: Jul. 1, 1997

§ 102(e) Date: Jul. 1, 1997

[87] PCT Pub. No.: WO96/14416

PCT Pub. Date: May 17, 1996

[30] Foreign Application Priority Data

Nov. 7, 1994 [FR] France ................................. 94 13310

[51] Int. Cl.$^7$ ........................ A61K 39/12; A61K 39/385; C12N 15/62; C07K 1/10; C07K 19/00
[52] U.S. Cl. .................................. 424/192.1; 424/196.11; 424/211.1; 424/212.1; 424/226.1; 424/227.1; 424/28.1; 530/403; 435/69.3; 435/320.1; 536/23.4
[58] Field of Search ............................. 424/190.1, 192.1, 424/193.1, 197.11, 282.1, 196.11, 211.1, 212.1, 226.1, 227.1, 228.1; 435/69.3, 69.7, 320.1; 530/350, 403, 23.4

[56] References Cited

U.S. PATENT DOCUMENTS 4,415,491 11/1983 Vyas.

FOREIGN PATENT DOCUMENTS

| 0 327 522 | 8/1989 | European Pat. Off. . | |
|---|---|---|---|
| 91/01743 | 2/1991 | WIPO | A61K 37/02 |
| WO91 16926 | 11/1991 | WIPO . | |
| WO92 01471 | 2/1992 | WIPO . | |
| WO93 06218 | 4/1993 | WIPO . | |

OTHER PUBLICATIONS

Boswell, D.R. et al. In: Computational Molecular Biology, ed. A.M. Lesk, Oxford University Press, Oxford, pp. 161–178, 1988.

Immunomethods; vol. 2, No. 1, Feb. 1993, pp. 79–92; Sjolander Et Al.; "Bacterial Expression Systems Based on Protein A and Protein G Designed for the Production of Immunogens: Applications to Plasmodium Falciparum Malaria Antigens".

Infection and Immunity; vol. 58, No. 4, Apr. 1990, pp. 854–859; Sjolander Et Al.; "Immunogenicity and Antigenicity in Rabbits of A Repeated Sequence of Plasmodium Falciparum Antigen PF155/RESA Fused to Two Immunoglobulin G–Binding Domains of Staphylococcal Protein A".

Database Medline; File Server STN Karlsruhe; 93202225; Sjolander Et Al.; "Plasmodium Falciparum: the Immune Response in Rabbits to the Clustered Asparagine–Rich Protein (CARP) After Immunization in Freund's Adjuvant or Immunostimulating Complexes (ISCOMS)"; Mar. 1993, 76 (2), 134–45.

Journal of Molecular Recognition; vol. 1, No. 2, Apr. 1988, pp. 69–74; Nygren Et Al.; "Analysis and Use of the Serum Albumin Binding Domains Of Streptococcal Protein G".

Database Chemical Abstracts; File Server STN Karlsruhe; Asbtract No. 124:84244; Berzins Et Al.; "Immunogenicity in Aotus Monkeys of ISCOM Formulated Repeat Sequences From the Plasmodium Falciparum Asexual Blood Stage Antigen PF155/RESA"; 1995, 4(3), 121–33.

*Primary Examiner*—Mary E. Mosher
*Attorney, Agent, or Firm*—Rockey, Milnamow & Katz

[57] ABSTRACT

The present invention relates to a process for improving the immunogenicity of an immunogen, an antigen or a hapten, when it is administered to a host, independently of the mode of administration, characterized in that the said antigen or hapten is coupled covalently to a support molecule in order to form a complex, and in that this support molecule is a polypeptide fragment which is able to bind specifically to mammalian serum albumin. The invention also relates to the use, as a medicament, of the product which can be obtained in this way.

46 Claims, 1 Drawing Sheet

METHOD FOR ENHANCING THE IMMUNOGENICITY OF AN IMMUNOGENIC COMPOUND OR HAPTEN, AND USE THEREOF FOR PREPARING VACCINES

RSV is the most frequent cause of the hospitalization of unweaned infants under one year old for acute respiratory infections. Infants suffering from laryngo-tracheobronchites, bronchiolites and pneumonias require hospital care, and the incidence of mortality in unweaned infants exhibiting congenital cardiac diseases is greater than 37%. Other disorders such as bronchopulmonary dysplasias, renal diseases and immunodeficiency are equally much factors which are responsible for increased mortality. Infections with RSV can also be a cause of death in old people.

In temperate countries, the RSV epidemic occurs during the winter period from November to April, and the highest incidence of serious diseases is found in the unweaned infant of 2 to 6 months. A distinction is made between two types of RSV, RSV-A and RSV-B, on the basis of the antigenic variation of the G glycoprotein of RSV: subgroup A and subgroup B, which circulate concurrently. A recent study which was carried out in France from 1982 to 1990 demonstrated the alternation of one subgroup with the other over a period of 5 years. Strain A is often the cause of infections which are more serious than those caused by strain B.

In the 1960's, an unsuccessful attempt was made to develop conventional vaccines, that is using formol-inactivated RSV, in analogy with anti-measles vaccines. Instead of conferring protection on the vaccinated infant, this type of vaccine had the effect of potentiating the natural viral disease.

Human RSV belongs to the genus pneumovirus, which is a member of the Paramyxoviridae family. The genome of the virus consists of an RNA strand which is of negative polarity, is nonsegmented and encodes 10 distinct proteins: NS1, NS2, N, P, M, SH (or 1A), G, F, M2 (or 22K) and L.

Numerous published experiments have demonstrated that the main proteins involved in protection are: F, G and N. The fusion glycoprotein F, which is synthesized as precursor $F_0$, is cleaved into two subunits F1 (48 kDa) and F2 (20 kDa) which are bound together by disulphide bridges. The F protein is conserved between RSV-A and RSV-B (91% homology). Conversely, the attachment glycoprotein G varies greatly from one subgroup to the other. Only one region of 13 amino acids (aa 164 to aa 176) is highly conserved and four cysteine residues (173, 176, 182 and 186) are preserved in each subgroup. It has been shown in animal models that the two glycoproteins F and G play a major role in the immunology of RSV. Monoclonal antibodies directed against G and F are able to neutralize the virus in vitro and, when administered passively, they protect the cotton rat from RSV infection.

Current treatments for aggravation of the disease caused by RSV in unweaned infants are clearing the respiratory tract of congestion by aspirating mucus and respiratory assistance provided by ventilation. An antiviral agent, ribavirin, appears to be effective in seriously affected cases. However, its use in paediatric therapy is still poorly defined. Passive immunization with anti-RSV immunoglobulins represents an alternative route in the treatment of serious RSV infections: no undesirable side-effect has been observed. Nevertheless, this type of treatment is very costly and difficult to extrapolate to a large scale.

Different approaches have been taken to vaccinating against human RSV: either the vaccine protects against RSV infection in animals (rodents and primates) but induces pulmonary pathology or else the vaccine is not sufficiently immunogenic and does not provide protection (Connors et al., Vaccine 1992; 10: 475–484).

For this reason, the present invention relates to a process for improving the immunogenicity of an immunogen, in particular an antigen, or a hapten, when it is administered to a host, independently of the mode of administration, characterized in that the said immunogen or hapten is coupled covalently to a support molecule in order to form a complex, and in that this support molecule is a polypeptide fragment which is able to bind specifically to mammalian serum albumin.

Administration can, in particular, take place enterally, parenterally or orally.

The immunogenicity of the complex between the immunogen and the support molecule is found to be improved as compared with that of the immunogen alone, in the absence of any other-immunostimulant.

A complex which is particularly suitable for implementing the present invention is obtained by using a conjugate with a polypeptide which is derived from the G protein of Streptococcus; this protein has been characterized by Nygren et al. (J. Mol. Recognit. 1988; 1:69–74).

The invention relates to a process in which the support molecule exhibits the amino acid sequence denoted sequence ID No: 74 or a sequence which exhibits at least 80%, and preferably at least 90%, homology with the said sequence ID No: 74.

This sequence can be attached to linking sequences which promote its expression in a host.

According to the invention, use can also be made of a support molecule which exhibits one of the sequences ID No: 75 or No: 78, as well as of molecules which exhibit at least 80%, and preferably at least 90%, homology with the said sequences.

The peptide sequence ID No: 78 exhibits the following characteristics:

| Sequence ID No: 78 Molecular weight: 26529 | | | | | | | |
|---|---|---|---|---|---|---|---|
| Gly: | 10 (4.08%); | Ala: | 30 (12.24%); | Ser: | 14 (6.12%); | | |
| Thr: | 16 (6.53%); | Val: | 20 (8.16%); | Leu: | 23 (9.39%); | | |
| Ile: | 12 (4.90%); | Pro: | 4 (1.63%); | Cys: | 0 (0.00%); | | |
| Met: | 1 (0.41%); | His: | 2 (0.82%); | Tyr: | 9 (3.67%); | | |
| Asp: | 19 (7.76%); | Glu: | 19 (8.16%); | Lys: | 27 (11.02%); | | |
| Arg: | 5 (2.04%); | Asn: | 16 (6.94%); | Gln: | 8 (3.27%); | | |
| Phe: | 7 (2.86%); | | | | | | |

The complex between the support molecule and the compound whose immunogenicity it is desired to improve can be produced by recombinant DNA techniques, in particular by inserting or fusing the DNA encoding the immunogen or hapten into the DNA molecule encoding the support.

According to another embodiment, the covalent coupling between the support molecule and the immunogen is effected chemically using techniques known to the person skilled in the art.

The invention also relates to a gene fusion which renders it possible to implement the process for improving the immunogenicity, characterized in that it comprises a hybrid DNA molecule which is produced by inserting or fusing the DNA encoding the immunogen or hapten into the DNA molecule encoding the support molecule and which is fused with a promoter; the invention also comprises a vector which contains such a gene, it being possible for the said vector to have, in particular, as its origin a DNA vector which derives from a plasmid, a bacterio-phage, a virus and/or a cosmid.

A vector which exhibits the sequence ID No: 76 or 77 belongs to the invention, as does the corresponding polypeptide. These polypeptides exhibit the following characteristics:

| Sequence ID No: 76 Molecular weight: 38681 | | | | | | | |
|---|---|---|---|---|---|---|---|
| Gly: | 11 (3.15%); | Ala: | 31 (8.88%); | Ser: | 18 (5.16%); | | |
| Thr: | 37 (10.60%); | Val: | 23 (7.16%); | Leu: | 23 (6.59%); | | |
| Ile: | 15 (4.30%); | Pro: | 19 (5.44%); | Cys: | 4 (1.15%); | | |
| Met: | 2 (0.57%); | His: | 4 (1.15%); | Tyr: | 9 (2.58%); | | |
| Asp: | 22 (6.30%); | Glu: | 22 (6.30%); | Lys: | 48 (13.75%); | | |
| Arg: | 7 (2.01%); | Asn: | 26 (7.45%); | Gln: | 13 (3.72%); | | |
| Phe: | 12 (3.44%); | Trp: | 1 (0.29%); | | | | |

| Sequence ID No: 77 Molecular weight: 39268 | | | | | | | |
|---|---|---|---|---|---|---|---|
| Gly: | 12 (3.37%); | Ala: | 31 (8.71%); | Ser: | 22 (6.18%); | | |
| Thr: | 37 (10.39%); | Val: | 26 (7.30%); | Leu: | 23 (6.46%); | | |
| Ile: | 15 (4.21%); | Pro: | 21 (5.90%); | Cys: | 2 (0.56%); | | |
| Met: | 2 (0.56%); | His: | 4 (1.12%); | Tyr: | 9 (2.53%); | | |
| Asp: | 23 (6.46%); | Glu: | 22 (6.18%); | Lys: | 48 (13.48%); | | |
| Arg: | 7 (1.97%); | Asn: | 26 (7.30%); | Gln: | 13 (3.65%); | | |
| Phe: | 12 (3.37%); | Trp: | 1 (0.28%); | | | | |

The DNA molecule which encodes the complex between the immunogen and the support molecule can be integrated into the genome of the host cell.

In one of its embodiments, the novel process includes a step for producing the complex, by genetic manipulation, in a host cell.

The host cell can be of the prokaryote type and be selected, in particular, from the group comprising: E. coli, Bacillus, Lactobacillus, Staphylococcus and Streptococcus; it can also be a yeast.

According to another aspect, the host cell is derived from a mammal.

The gene fusion which encodes the complex having an improved immunogenicity can, in particular, be introduced into the host cell by the mediation of a viral vector.

The immunogen which is used preferably derives from bacteria, parasites and viruses.

This immunogen can be a hapten: peptide or polysaccharide.

The novel process is particularly suitable for a surface polypeptide from a pathogen. When this polypeptide is expressed in the form of a fusion protein, using recombinant DNA techniques, the fusion protein is advantageously expressed, anchored and exposed at the surface of the membrane of the host cells. Nucleic acid molecules are employed which are able to direct the synthesis of the antigen in the host cell.

They comprise a promoter sequence, a functionally linked secretion signal sequence and a sequence which encodes a membrane anchoring region, which sequences will be adapted by the person skilled in the art.

The immunogen can, in particular, be derived from an RSV surface glycoprotein: F and/or G.

Particularly advantageous results are obtained using fragments of the G protein from RSV subgroups A or B.

The proteins which are derived from the G glyco-protein of RSV subgroup A and subgroup B can be genetically fused or chemically coupled to BB.

The invention relates, therefore, to a complex which is obtained using the sequence which is encompassed between amino acids 130 and 230 of the G protein of RSV, or a sequence exhibiting at least 80% homology with the said sequence of the G protein.

This sequence can be obtained from human or bovine RSV which belongs to subgroups A or B.

The sequence encompassed between amino acids 130 and 230 of the G protein can be subjected to various types of modification for the purpose of modulating its immunogenic activity and its expression by the host system.

The applicant has, in particular, demonstrated that polypeptides are of interest in which:

the Cys amino acid in positions 173 and/or 186 has been replaced by an amino acid which does not form a disulphide bridge, in particular serine, and/or the amino acids in positions 176 and 182 are capable of forming a covalent bridge other than a disulphide bridge, in particular aspartic acid and ornithine, and/or the phenylalanine amino acids corresponding to positions 163, 165, 168 and/or 170 of the sequence of the G protein are replaced by a polar amino acid, in particular serine, and/or the sequence encompassed between the amino acids numbered 162 and 170 is deleted.

Peptides exhibiting one-of the sequences ID No: 1 to 73, or a sequence possessing at least 90% homology with one of the sequences ID No: 1 to 73, are thus particularly suitable for implementing the invention.

Other immunogens which are suitable for implementing the novel process include a derivative of the surface protein of hepatitis virus A, B and C, a surface protein of the measles virus, a surface protein of parainfluenza virus 3, in particular a surface glycoprotein such as haemagglutinin, neuraminidase HN and fusion protein F.

The RNA or DNA nucleotide sequences which encode complexes such as those previously defined, and which include elements which enable expression to be targeted in certain specific host cells, are included in the invention. They can be incorporated into a viral or plasmid vector; this vector will be administered to a mammal, in particular within a pharmaceutical composition, in order to enable the complex between the immunogen and the support molecule to be produced in situ.

The invention also relates to the use of a gene fusion or a complex between an immunogen (P) and a support molecule, such as those previously defined, as a medicament. The pharmaceutical compositions containing the gene or the complex together with physiologically acceptable excipients also belong to the invention. They are particularly suitable for preparing a vaccine.

Immunization can be obtained by administering the nucleotide sequence either on its own or through the agency of a viral vector. The host cell, in particular an inactivated bacterium, may also be used. Finally, the complex which is obtained by chemical coupling or is in the form of a fusion protein induces an antibody response which is very powerful compared with that induced by (P) on its own coupled to Freund's adjuvant.

Within the scope of a vaccine against RSV, the applicant has demonstrated the ef ficacy of the fusion protein BBG2A, where G2A is a 101 amino acid fragment of the G protein of RSV-A (G aa 130–aa 230), se(id No. 1. When used to immunize rodents, BBG2A and BBG2AδC coupled to alum (aluminium hydroxide) confer complete protection against challenge with RSV-A (Long strain).

The examples which follow are intended to illustrate the invention without limiting its scope in any way.

In these examples, reference will be made to the following figure:

FIG. 1: Construction of pVABBG2(A).

EXAMPLE 1

Cloning Genes G2A and G2AδC Into Expression Vector PVABB308 and Producing Fusion Proteins BBG2A and is BBG2AδC in *Escherichia Coli*

1) Expression vector pVABB308

The *E. coli* expression vector pVABB308 (5.4 kbp) encompasses the tryptophan operon promoter (Trp), followed by the gene encoding the human albumin-binding region BB, originating from the G protein of Streptococcus (Nygren et al., J. Mol. Recognit. 1988; 1: 69–74) and a multiple cloning site, mp8, into which various heterologous genes can be inserted (see FIG. 1). Plasmid pVABB308 contains an ampicillin resistance gene (AMP), a tetracycline resistance gene (Tet) and the *E. coli* origin of replication. Expression of the gene is induced by adding IAA. (indoleacrylic acid) to the *E. coli* culture medium during the exponential growth phase.

2) Cloning the genes G2A and G2AδC into PVABB308

2.1. BBG2A

The gene encoding RSV-A G (130-230) was obtained by the method of assembling synthetic genes in solid phase (in accordance with Stahl et al., Biotechniques 1992: 14: 424–434) and cloned into expression vector pVABB using the EcoRI and HindIII restriction sites. The resulting vector is termed pVABBG2A (5791 bp). The fusion product BBG2A is purified in two forms from the cytosol of *E. coli* which has been transformed with vector pVABBG2A:

a soluble form, BBG2A (sol), following cell disintegration and centrifugation; the supernatant containing the soluble proteins is loaded directly onto an affinity column.

The products are recovered after eluting at acid pH.

an insoluble form, BBG2A (insoluble), which is obtained after renaturing, in an oxidizing medium, the inclusion bodies which have been dissolved in a chaotropic agent (guanidine HCl) (31, 93), and is then subjected to affinity purification.

2.2. BBG2AδC

The two cysteine residues (173 and 186) are replaced by serines (Ser). When the genes are being assembled, the oligonucleotide which encompasses the 2 Cys residues which are encoded by the (TGC) triplet is quite simply replaced by another oligonucleotide in which one of the nucleotides has been changed: (TCC) encoding Ser). We wished deliberately to modify one disulphide bridge in this version in order exclusively to retain the disulphide bridge which is formed by Cys residues (176 and 182) and which is critical for protection (Trudel et al., Virology 1991; 185: 749–757).

We introduced a Met residue between the BB affinity tail and G2A or BB and G2AδC: BB-Met-G2A and BB-Met-G2AδC, thereby rendering it possible to cleave the fusion product chemically using cyanogen bromide (CNBr); the mixture is passed through an HSA-Sepharose affinity column. The cleaved peptide, G2A (G2AδC), is not bound and is therefore recovered in the eluate and then purified by reverse phase HPLC.

3) Fermentation and purification of fusion proteins

Two Erlenmeyer flasks containing 250 ml of TSB (tryptic soy broth, Difco) together with ampicillin (100 μg/ml, Sigma) and tetracycline (8 μg/ml, Sigma) are inoculated with *E. coli* RV308 strains which are transformed with plasmids pVABBG2A and pVABBG2AδC, respectively. The flasks are incubated, with shaking, at T°=32° C. for 16 hours. 200 ml of this culture are inoculated into a fermenter (CHEMAP CF3000, ALFA LAVAL) which contains 2 litres of culture medium. The medium contains (g/l)=glycerol, 5; ammonium sulphate, 2.6; potassium dihydrogen phosphate, 3; dipotassium hydrogen phosphate, 2; sodium citrate, 0.5; yeast extract, 1; ampicillin, 0.1; tetracycline, 0.008; thiamine, 0.07; magnesium sulphate, 1, and 1 ml of a trace element solution/l and 0.65 ml of a vitamin solution/l. The parameters which are monitored during the fermentation are: pH, shaking, temperature, oxygenation rate and supply of carbon sources (glycerol or glucose). The pH is maintained at 7.3. The temperature is kept at 32° C. Growth is controlled by supplying glycerol at a constant rate in order to keep the tension signal of dissolved oxygen at 30%. When the turbidity of the culture (measured at 580 nm) reaches a value of 80 (after about 27 hours of culture), production of the proteins is induced by adding indoleacrylic acid (IAA) to a final concentration of 25 mg/l. Three hours after the induction, the cells are harvested by centrifugation. The biomass yields which are obtained are of the order of 150 g/l of culture.

A fraction of 30 g of moist biomass is resuspended in 70 ml of TST solution (50 mM Tris-HCl, pH 8.0, 200 mM NaCl, 0.05°% Tween 20 and 0.05 mM EDTA). These cells are disintegrated by sonication (Vibracell 72401, Sonics & Materials). After the cell lysate has been centrifuged, the supernatant is filtered (1.2 μm) and diluted in 500 ml of TST. The fusion proteins thus obtained in soluble form are purified on an affinity column: HSA-Sepharose (human serum albumin) in accordance with the protocol described by Stahl et al. (J. Immunol. Methods, 1989; 124: 43–52).

After it has been centrifuged, the insoluble lysate is washed once with a buffer (50 mM Tris-HCl, pH 8.5; 5 mM MgCl$_2$). After the wash, the pellet is solubilized in 30 ml of 7 M guanidine hydrochloride, 25 mM Tris-HCl (pH 8.5), 10 mM dithiothreitol (DTT), with the mixture then being incubated at 37° C. for 2 hours. The solubilized proteins are added to a renaturation buffer (25 mM Tris-HCl (pH 8.5); 150 mM NaCl; 0.05% Tween 20). The concentration of the guanidine hydrochloride is adjusted to a final concentration of 0.5 M in the renaturation buffer before adding the solubilized fusion proteins. The mixture is incubated at room temperature for 16 hours with gentle stirring. Following centrifugation, the soluble fusion products in the supernatant are purified on an HSA-Sepharose column. The purified fusion proteins are analysed on an SDS-PAGE gel (12%) under reducing conditions using a MINI PROTEAN II SYSTEM (BIORAD) appliance. The proteins are visualized with Coomassie brilliant blue R250.

EXAMPLE 2

Carrier Effect of the BB Polypeptide and Immunogenicity of BBG2AδC

1. Immunization protocol

C57B1/6 mice (5 per batch) were given 2 subcutaneous injections of the equivalent of 10 μg of G2AδC in the presence of Freund's adjuvants on D0 (complete adjuvant) and D14 (incomplete adjuvant). On D21, the sera were tested individually by ELISA for the production of G2AδC- specific antibodies. The antibody titre is determined as being the inverse of the serum dilution which gives twice the absorbance of the serum of the animal prior to immunization. The results which are presented are the arithmetic mean of the anti-G2AδC antibody titres which were obtained for each of the batches.

RESULTS TABLE

| ANTIGEN | Mean titre of anti-G2AδC antibody |
|---|---|
| 1) G2AδC + FA | 180 |
| 2) BBG2AδC + FA | 92 800 |
| 3) G2AδC + BB + FA | 1 200 |

2. Results

The above table demonstrates that G2Aδc is a weak immunogen even in the presence of Freund's adjuvant. The BB protein has a poor adjuvant ability since, when it has been added to G2AδC, the anti-G2AδC antibody titre is only increased by 1 log. On the other hand, fusing BB to G2AδC increases the anti-G2AδC antibody production by about 3 logs.

We may conclude, therefore, that BB is an excellent carrier protein for G2AδC and that the fusion protein BBG2AδC is very immunogenic.

EXAMPLE 3

Study of the Protection Induced By Fusion Proteins BBG2A and BBG2AδC in Rodents a) Study protocols Female BALB/c mice and cotton rats (Sigmodon hispidus) (IFFA-CREDO), which are animal models for RSV infection, are employed in the immunization experiments.

The animal groups are given 1, 2 or 3 doses of 200 μg, 20 μg, 2 μg or 0.2 μg of RSV-A candidate vaccine in 20% aluminium hydroxide $(Al(OH)_3)$ (v/v) at 2-week intervals. The mice are immunized by the intraperitoneal (i.p.) route while the cotton rats are immunized with intramuscular (i.m.) injections. The control groups are given $10^5$ $TCID_{50}$ of RSV-A or PBS-A (PBS without $Ca^{2+}$ or $Mg^{2+}$) in 20% aluminium hydroxide (v/v).

Three to four weeks after the last immunization, the animals are challenged by the intranasal (i.n.) route with approximately $10^5$ $TCID_{50}$ RSV-A. They are sacrificed 5 days later following intracardiac blood puncture. The presence of the virus in their lungs is determined in accordance with Trudel et al. (Virology 1991; 185; 749–757).

The different products which are tested are BBG2A, BBG2AδC and BB alone.

b) Results table

TABLE 3.1

| | Protection results in rodents | | | |
|---|---|---|---|---|
| | Mice | | Cotton rats | |
| Antigens | Protection* | Complete protection° | Protection | Complete protection |
| BBG2A | 41/41+ | 38/41 | 22/22 | 22/22 |
| BBG2AδC | 32/34 | 27/34 | 8/13 | 7/13 |
| BB | 0/20 | 0/20 | 0/3 | 0/3 |
| RSV-A | 28/28 | 28/28 | 17/17 | 17/17 |
| PBS-A | 0/29 | 0/29 | 0/21 | 0/21 |

*Protection = a reduction of virus in the lungs of $\geq \log_{10} 2$ as compared with the mean virus titre in the lungs of mice immunized with PBS-A.
°Complete protection = no virus detected in the lungs.
+ X/Y where X = number of animals protected or completely protected; Y = number of animals tested

TABLE 3.2

| | Details of protection in the mouse | | | | | |
|---|---|---|---|---|---|---|
| | 3 doses of antigen | | 2 doses of antigen | | 1 dose of antigen | |
| | BBG2A | BBG2δC | BBG2A | BBG2δC | BBG2A | BBG2δC |
| 200 μg/dose | | | | | | |
| Protection* | 9/9+ | 9/9 | 4/4 | 4/4 | 4/4 | 2/4 |
| Complete protection° | 9/9 | 8/9 | 4/4 | 3/4 | 3/4 | 1/4 |
| 20 μg/dose | | | | | | |
| Protection* | 4/4 | 4/4 | 3/3 | NT | NT | NT |
| Complete protection° | 4/4 | 4/4 | 2/3 | NT | NT | NT |
| 2 μg/dose | | | | | | |
| Protection* | 4/4 | 4/4 | 2/2 | NT | NT | NT |
| Complete protection° | 3/4 | 3/4 | 2/2 | NT | NT | NT |
| 0.2 μg/dose | | | | | | |
| Protection* | 4/4 | 4/4 | NT | NT | NT | NT |
| Complete protection° | 4/4 | 3/4 | NT | NT | NT | NT |

*Protection = a reduction of virus in the lungs of $\geq \log_{10} 2$ as compared with the mean virus titre in the lungs of mice immunized with PBS-A.
°Complete protection = no virus detected in the lungs.
+ X/Y where X = number of mice protected or completely protected; Y = number of mice tested
NT = Not tested Results of the immunological tests in mice

TABLE 3.3

| Antigens | ELISA (mean LOG$_{10}$) | Neutralizing antibodies (mean titre/25 µl) |
|---|---|---|
| BBG2A | 5.09 (28) | ≧512 (15) |
| BBG2AδC | 3.71 (29) | ≧256 (12) |
| RSV-A | 5.32 (21) | ≧512 (12) |

( ) = number of animals tested c) Discussion

The experimental protection results are presented in Tables 3.1. and 3.2. Each molecule was tested in at least 2 independent experiments. The results clearly demonstrate that BBG2A protects rodents against a pulmonary infection with RSV-A independently of the immunization protocol which was employed. Under our experimental conditions, a single injection of 200 µg, 2 injections of 2 µg, or 3 injections of only 0.2 µg of BBG2A are sufficient to protect the mice against infection (Table 3.2). Virus was detected in a third animal of the same group but at the limit of detection. These results suggest that BBG2A displays a potential and an efficacy which are very comparable to those of RSV-A in the immunized control animals and to those of the RSV-A subunit candidate vaccines which are described in the literature.

BBG2AδC was also effective in mice, protecting 32 animals out of 34 against pulmonary infection. Two doses of 200 µg were found to be effective, just as were 3 injections of 0.2 µg. Thus, in these immunization protocols consisting of several injections, BBG2AδC was shown to be comparable in its activity and efficacy in mice to the already described RSV-A sub unit candidate vaccines.

The results of the immunological tests of the humoral and cellular response in BALB/c mice are presented in Table 3.3. In general, the mean titres of anti-RSV-A-specific antibodies which are obtained by the ELISA technique are considered to be one of the parameters reflecting the protective activity of the candidate vaccines. The sera of the mice immunized with RSV-A consistently demonstrated elevated anti-RSV-A antibody titres. The virus was never detected in the lungs of these animals. The mice immunized with BBG2A exhibited mean titres of anti-RSV-A antibodies which were similarly elevated and were always protected when challenged with RSV-A.

The mean anti-RSV-A antibody titres induced with BBG2AδC were lower than those obtained with the molecules mentioned above. Furthermore, the animals which were immunized with this molecule exhibited slightly reduced protection. Even if the sera of some animals which were immunized with BBG2AδC exhibited very low titres of anti-RSV-A-specific antibodies (data not shown), certain of these animals were nevertheless completely protected when challenged with RSV-A.

The protection studies demonstrate the protective efficacy of the anti-RSV-A subunit candidate vaccines. Two molecules, BBG2A and BBG2AδC, were found to be very effective in two rodent models for RSV-A infection during challenge with the homologous virus.

EXAMPLE 4

Immunogenic and Protective Efficacy of BBG2AδC as Compared With G2AδC in the BALB/c Mouse.

Materials and methods:

Groups of 4 BALB/c mice, which were seronegative with regard to RSV-A, were immunized twice at an interval of 2 weeks, by intraperitoneal (i.p.) injections, with 5.1, 0.51 and 0.051 nM of BBG2AδC and G2AδC. The latter molecule is derived by chemically cleaving BBG2AδC with cyanogen bromide. A group of 3 mice was immunized twice at an interval of 2 weeks with PBS buffer in order to serve as negative controls. Alhydrogel (Al(OH)$_3$) (20° v/v) (Superfos BioSector, Denmark) was employed as adjuvant for all the immunizations. A blood puncture was carried out 2 weeks after the last immunization in order to determine the ELISA titres against G2AδC. The mice were challenged with RSV-A (10$^5$ TCID$_{50}$) at 3 weeks after the last immunization. They were sacrificed 5 days later and subjected to cardiac puncture in order to titrate the post-challenge anti-RSV-A antibodies, and the lungs were removed in order to titrate the pulmonary RSV-A.

Results:

See Table 4.

The anti-G2AδC ELISA results indicate that BBG2AδC is always more immunogenic than G2AδC whatever dose (0.051–5.1 nM) is administered. Especially at 0.051 nM, BBG2AδC induces a mean anti-G2AδC titre of log$_{10}$ 3.27 whereas the same concentration of G2AδC does not induce any detectable anti-G2AδC antibodies. The same applies as far as the anti-RSV-A ELISAs are concerned; 4 mice out of 4 which were immunized with 5.1 or 0.51 nM of BBG2AδC were seropositive, with the mean titres being log1$_{10}$ 2.67 and 2.78, respectively. However, two mice out of 4 which were immunized with 5.1 nM of G2AδC were seropositive, with one being at the limit of detection of the assay and one having a mean titre of log$_{10}$≦2.19. The mice immunized with 0.51 or 0.051 nM of G2AδC did not show evidence of anti-RSV-A antibodies.

The lungs of all the mice which were immunized with 5.1 or 0.51 nM of BBG2AδC were protected against a challenge with the homologous virus. Except for one mouse which was immunized with 0.51 nM of BBG2AδC, which only exhibited virus at the limit of detection of the method, the presence of pulmonary virus was not demonstrated in any of the animals. Following immunization with 0.051 nM of BBG2AδC, 3 mice out of 4 were protected, with 2 of the mice having no evidence of pulmonary virus. In the fourth mouse, the pulmonary virus was diminished by the order of log$_{10}$ 1.16 as compared with the mean titre of the controls immunized with PBS-A.

The lungs of three mice out of 4 which were immunized with 5.1 nM of G2AδC were protected against a challenge with RSV-A. The pulmonary virus in the fourth mouse was diminished by the order of log$_{10}$ 1.75 as compared with the mean titre of the controls immunized with PBS-A buffer. In only one of the protected mice was pulmonary virus not detected. The same results are observed after immunizing with 0.51 nM of G2AδC, apart from one unprotected mouse which did not exhibit any significant diminution in pulmonary virus as compared with the controls immunized with PBS-A buffer. The lower respiratory tracts of the mice immunized with 0.051 nM of G2AδC were not protected against a challenge with the homologous virus.

Conclusions:

The results indicate that, in accordance with the conditions of this study, BBG2AδC is of the order of 10 to 100 times as effective as G2AδC in inducing immune responses which protect the lungs against a challenge with RSV-A.

TABLE 4

Comparative efficacy of the immunogenicity and protection induced in BALB/c mice which are immunized with BBG2AδC or G2AδC.

| Concentration of immunogen (nM) | ELISA titre ($\log_{10}$) | | | | % protected animals | | $\log_{10}$ TCID$_{50}$ RSV-A/g of lung | |
|---|---|---|---|---|---|---|---|---|
| | vs G2AδC | | vs RSV-A | | | | | |
| Immunized with = | BBG2AδC | G2AδC | BBG2AδC | G2AδC | BBG2AδC | G2AδC | BBG2AδC | G2AδC |
| 5.1 | 5.06 ± 0.27 | 4.70 ± 0.46 | 2.67 ± 0.83 | ≦2.19 ± 0.48 | 100 | 25 | <1.53 ± 0.12 | ≦1.80 ± 0.35 |
| 0.51 | 4.46 ± 0.46 | 3.86 ± 0.59 | 2.78 ± 0.60 | <1.95 ± 0.00 | 75 | 25 | ≦1.47 ± 0.04 | ≦1.97 ± 0.99 |
| 0.051 | 3.27 ± 1.53 | ≦1.95 ± 0.00 | ≦2.19 ± 0.48 | <1.95 ± 0.00 | 50 | 0 | ≦1.93 ± 0.67 | 4.08 ± 0.48 |
| PBS-A | — | | 1.95 ± 0.00 | | 0 | | 4.03 ± 0.29 | |

TABLE 5

Protective efficacy of the vaccine candidates in BALB/c mice against a challenge with RSV-A.

| Product | $\log_{10}$ TCID$_{50}$RSV-A/ g of lung | ELISA titres ($\log_{10}$) | | |
|---|---|---|---|---|
| | | P. Im* vs antigen | P. Im vs RSV-A | P. Ch* vs RSV-A |
| 20 μg BBG7a | <1.45 ± 0.00 | 6.25 ± 0.00 | 3.38 ± 0.00 | 3.38 ± 0.00 |
| 20 μg BBG200a | <1.45 ± 0.00 | 6.41 ± 0.28 | 4.66 ± 0.28 | 4.66 ± 0.28 |
| 20 μg BBG198a | <1.45 ± 0.00 | 6.09 ± 0.28 | 4.66 ± 0.28 | 4.58 ± 0.35 |
| 20 μg BBG196a | <1.45 ± 0.00 | 5.93 ± 0.28 | 4.34 ± 0.00 | 4.18 ± 0.28 |
| 20 μg BBG194a | <1.45 ± 0.00 | 5.77 ± 0.00 | 4.34 ± 0.48 | 4.34 ± 0.48 |
| 20 μg BBG192a | <1.45 ± 0.00 | 5.77 ± 0.00 | 3.54 ± 0.28 | 3.86 ± 0.00 |
| PBS-A | 3.74 ± 0.29 | — | 2.03 ± 0.20 | 1.95 ± 0.00 |
| RSV-A | <1.45 ± 0.00 | — | 4.82 ± 0.00 | 4.82 ± 0.00 |

*P. Im. = ELISA results post-immunization but before challenge.
*P. Ch. = ELISA results in sera removed by cardiac puncture at the time of sacrifice.

EXAMPLE 5

Protective Efficacy of the Vaccine Candidates in BALB/c Mice Against a Challenge With RSV-A.

Materials and methods:

Groups of 3 mice were immunized twice at an interval of 2 weeks with 20 μg of the following products:

BBG7A, BBG200A, BBG198A, BBG196A, BBG194A and BBG192A

Two groups of 6 and 4 mice were immunized twice at an interval of 2 weeks with PBS-A and RSV-A ($10^5$ TCID$_{50}$), respectively, as controls. Alhydrogel (Al(OH)$_3$) (20% v/v) was employed as adjuvant for each immunization. All the animals were sampled from the eye before the first immunization in order to verify their seronegativity with respect to RSV-A. All were seronegative or had titres at the detection limit of the ELISA assay. Two weeks after the second immunization, they were sampled from the eye in order to confirm their seroconversion with respect to the antigens and RSV-A. Three weeks after the last immunization, the mice were challenged by the intranasal route with $10^5$ TCID$_{50}$ of RSV-A. The mice were sacrificed 5 days after the challenge: they were subjected to cardiac puncture; the lungs were removed in order to titre the virus in the lower respiratory tracts. The post-challenge sera were tested by ELISA against the viral antigens.

Results:

See Table 5.

The mice which were immunized with BBG200A, BBG198A, BBG196A, BBG1194A, BBG192A and BBG7A were protected against a challenge with RSV-A without any evidence of virus in the lungs. All the products induced high mean antibody titres against the immunization antigen ($\log_{10}$ 5.77–6.41) and RSV-A ($\log_{10}$ 3.38–4.66).

These results are in agreement with those obtained from mice which were immunized with RSV-A.

Conclusions:

The above molecules are very immunogenic and induce immune responses which are able to protect the lungs of the BALB/c mouse against a challenge with RSV-A.

They therefore constitute potential vaccine candidates against RSV-A.

EXAMPLE 6

Protective Efficacy of BB-G4A in the BALB/c Mouse Against a Challenge With RSV-A.

Materials and methods:

Two groups of 3 mice were immunized twice at an interval of 2 weeks with 20 μg of BB-G4A or TT-G4A. The molecules are obtained by chemically coupling the peptide G4A (residues 172–187) onto the carrier proteins (either BB or TT). Two groups of 6 and 4 mice were immunized twice at an interval of 2 weeks with PBS-A and RSV-A ($10^5$ TCID$_{50}$), respectively, as controls. Alhydrogel (Al(OH)$_3$) (20% v/v) was employed as adjuvant for each immunization. All the animals were sampled from the eye before the first immunization in order to verify their seronegativity with regard to RSV-A. All were seronegative or had titres at the detection limit of the ELISA assay. Two weeks after the 2nd immunization, they were sampled from the eye in order to confirm their seroconversion with respect to the antigens and RSV-A. Three weeks after the last immunization, the mice were challenged by the intranasal route with $10^5$ TCID$_{50}$ of RSV-A. The mice were sacrificed 5 days after the challenge: they were subjected to a cardiac puncture; the lungs were removed in order to titrate the virus in the lower respiratory tracts. The post-challenge sera were tested by ELISA against the viral antigens.

Results:

BB-G4A, a protein which is obtained by coupling the peptide G4A to BB, protected the mice without any evidence of pulmonary virus. TT-G4A, a protein which is obtained by coupling the peptide G4A to TT, was less effective than BB-G4A as regards protecting the lungs; 2 mice out of 3 were protected, in this case, in one of which there was no evidence of pulmonary virus. The diminution in the virus count in the non-protected mouse was of the order of $\log_{10}$ 1.52 as compared with the controls immunized with PBS-A. The carrier:peptide ratios for BB-G4A and TT-G4A are ~1:7 and ~1:21, respectively. These results indicate, therefore, that BB is a better carrier for G4A than is TT.

The 2 products introduced high titres of antibodies against the immunization antigen ($\log_{10}$ 5.77 and 6.73, respectively, for the anti-BB-G4A and anti-TT-G4A sera post-immunization). By contrast, the animals which were immunized with these candidate vaccines had very low anti-RSV-A titres ($\log_{10}$ 2.11±0.28 and 2.43±0.48, respectively, for the anti-BB-G4A and anti-TT-G4A sera post-immunization).

Conclusions:

BB-G4A is able to protect the mice against a challenge with RSV-A without any evidence of pulmonary virus. It therefore confirms its potential as an anti-RSV-A vaccine. The results also indicate that BB is a better carrier for G4A than is TT.

TABLE 6

Protective efficacy of BB-G4A in the BALB/c mouse against a challenge with RSV-A.

| Product | $Log_{10}$ $TCID_{50}$RSV-A/g of lung | ELISA titres ($log_{10}$) P. Im* vs antigen | P. Im vs RSV-A | P. Ch* vs RSV-A |
|---|---|---|---|---|
| 20 μg BB-G4A | <1.45 ± 0.00 | 5.77 ± 0.00 | 2.11 ± 0.28 | 1.95 ± 0.00 |
| 20 μg TT-G4A | ≦1.78 ± 0.38 | 6.41 ± 0.28 | 2.43 ± 0.48 | 2.27 ± 0.55 |
| PBS-A | 3.74 ± 0.29 | — | 2.03 ± 0.20 | 1.95 ± 0.00 |
| RSV-A | <1.45 ± 0.00 | 4.82 ± 0.00 | 4.82 ± 0.00 | |

*P. Im. = ELISA results post-immunization but before challenge.
P. Ch. = ELISA results in the sera removed by cardiac puncture at the time of sacrifice.

EXAMPLE 7

Cross-Protection of the Lungs of BALB/c Mice Which Have Been Immunized With BBG2A by the Intraperitoneal Route With Respect to a Heterologous Challenge With RSV-B (Strain 8/60).

Materials and methods:

BALB/c mice were immunized twice or three times at 2-week intervals with 20 μg of BBG2A by means of intraperitoneal injection. Another group of mice were immunized in the same way with PBS-A as controls. Alhydrogel ($Al(OH)_3$) (20% v/v) was employed as adjuvant for each immunization. A blood sampling was carried out before the first immunization in order to verify their seronegativity with regard to RSV-A. Three weeks after the last immunization, the mice were challenged intranasally with $10^5$ $TCID_{50}$ of RSV-A or with $10^5$ $TCID_{50}$ of RSV-B. The mice were sacrificed 5 days after the challenge: they were subjected to cardiac puncture; the lungs were removed in order to titrate the virus in the lower respiratory tracts. The post-challenge sera were tested by ELISA against the viral antigens.

Results:

All the mice were seronegative for RSV-A at the beginning of the study. The first group, 11 mice out of 11, which were immunized with 20 μg of BBG2A, were protected with respect to a challenge with RSV-A. The second group, 11 mice out of 11, were also protected with respect to a heterologous challenge with RSV-B (Table 7).

Conclusions:

The immunization of BALB/c mice with the BBG2A antigen confers protection not only against RSV-A but also with respect to a challenge with RSV-B. Antigen BBG2A therefore induces cross-protection with respect to a heterologous challenge.

TABLE 7

Cross-protection of the lungs of BALB/c mice which are immunized intraperitoneally with BBG2A.

| | Challenge with RSV-A | | | Challenge with RSV-B | | |
|---|---|---|---|---|---|---|
| | $Log_{10}$ $TCID_{50}{}^1$/g of lung | % protection[b] | Number of immunized animals | $Log_{10}$ $TCID_{50}$/g of lung | % protection | Number of immunized animals |
| 20 μg BBG2A | <1.45[c] ± 0.00 | 100 | 11 | 1.68 ± 0.36 | 100 | 11 |
| PBS-A | 4.08 ± 0.60 | 0 | 4 | 4.25 ± 0.27 | 0 | 5 |

$TCID_{50}{}^a$ = tissue culture infectious dose 50

% protection[b] = a reduction in virus in the lungs of ≧$\log_{10}$ 1.8 as compared with the mean virus titre in the lungs of mice immunized with PBS-A.

<1.45[c] = limit of virus detection in this assay.

EXAMPLE 8

Study of the Priming Effect BB on Immun With BBG2A

BALB/c mice are sensitized to the BB protein are then given an injection of BBG2A. The anti-G2A titres obtained in these animals are compared with those obtained in mice which are given two injections of BBG2A.

Material and methods

BALB/C mice (N=5/batch) are immunized subcutaneously as described below:

|   | D0 | D14 |
|---|---|---|
| batch 1 | 0.1 ml PBS | 0.1 ml PBS |
| batch 2 | 20 μg BBG2A + FCA | 20 μg BBG2A + FIA |
| batch 3 | 100 μg BB + FCA | 20 μg BBG2A + FIA |

FCA: Freund's complete adjuvant;
FIA: Freund's incomplete adjuvant

The blood of the animals is sampled on D7 and D21 and the serum titres of anti-G2A IgM and IgG are determined individually by ELISA.

Results

Table of anti-G2A IgG titres

|   | D7 | | D21 | |
|---|---|---|---|---|
|   | BATCH 2 | BATCH 1 | BATCH 2 | BATCH 3 |
| M1 | 2 | 2 | 3.81 | 3.51 |
| M2 | 2 | 2 | 3.81 | 4.11 |
| M3 | 2 | 2 | 3.81 | 4.41 |
| M4 | 2 | 2 | 4.41 | 3.51 |
| M5 | 2 | 2 | 3.81 | 4.71 |
| m + σ | 2 | 2 | 3.93 ± 0.27 | 4.05 ± 0.54 |

In summary, the table of anti-G2A IgG titres at D7 and D21 is as follows:

|   | D0 | D7 | D14 | D21 |
|---|---|---|---|---|
| batch 1 | 0.1 ml PBS | — | 0.1 ml PBS | 2 |
| batch 2 | 20 μg BBG2A + FCA | 2 | 26 μg BBG2A + FIA | 4.93 ± 0.27 |
| batch 3 | 100 μg BB + FCA | — | 20 μg BBG2A + FIA | 4.05 ± 0.54 |

BATCH 2: 2 injections of BBG2A

Anti-G2A IgG is not detected at one week after the first injection of 20 μg of BBG2A. On the other hand, there is a strong production of anti-G2A IgG, approximately 4 $\log_{10}$, at one week after the second injection of BBG2A.

BATCH 3: Injection No. 1=BB, injection No. 2=BBG2A

After the mice have been sensitized with 100 μg of BB, one injection of 20 μg of BBG2A is sufficient to induce an anti-G2A IgG titre of 4 $\log_{10}$, which is a titre which is similar to that obtained with 2 injections of 20 μg of BBG2A.

Conclusion:

These results demonstrate that BB induces the production of Th memory cells which supplied the help required to the G2A-specific B cells at the time of the primary immunization with BBG2A, resulting in a secondary response of the IgG type. Thus, naive B cells can therefore be stimulated to produce anti-G2A antibodies.

BB thus supplies the T-cell help which is appropriate for producing antibodies directed against G2A; in this respect, it behaves as a carrier protein.

What is claimed is:

1. A process for improving the immunogenicity of an immunogen comprising covalently coupling an immunogen to a support molecule to form a complex, wherein said support molecule is a polypeptide fragment which binds specifically to mammalian serum albumin, and wherein said immunogen is derived from a surface glycoprotein selected from the group consisting of RSV surface glycoprotein F, RSV surface glycoprotein G, surface protein of hepatitis virus A, surface protein of hepatitis virus B, surface protein of hepatitis virus C, surface protein of the measles virus, surface protein of parainfluenza virus 3 and combinations thereof.

2. A process according to claim 1, characterized in that the polypeptide fragment is derived from the G protein of Streptococcus.

3. A process according to claim 1, characterized in that the support molecule is encoded by the sequence as set forth in SEQ ID NO: 74 or a sequence which is at least about 80% identical with SEQ ID NO: 74.

4. A process according to claim 1, characterized in that said covalent coupling is effected chemically.

5. A process according to claim 1 further comprising a step in which a gene fusion is introduced into a host cell, said gene fusion comprising a hybrid DNA molecule which is produced by inserting or fusing the DNA encoding said immunogen into DNA encoding said support and which is fused with a promoter.

6. A process according to claim 5, characterized in that the gene fusion is introduced with the agency of a DNA vector, which is derived from a plasmid, a bacteriophage, a virus and/or a cosmid.

7. A process according to claim 6, characterized in that a viral vector is employed.

8. A process according to claims 5, characterized in that the gene fusion is integrated into the genome of the host cell.

9. A process according to claim 5, characterized in that the host cell is a prokaryote.

10. A process according to claim 9, characterized in that the host cell is selected from the group comprising: *E. coli*, Bacillus, Lactobacillus, Staphylococcus and Streptococcus.

11. A process according to claim 5, characterized in that the host cell is a yeast.

12. A process according to claim 5, characterized in that the host cell is a mammalian cell.

13. A process according to claim 5, characterized in that the fusion molecule is expressed, anchored and exposed at the membrane of the host cells.

14. A sequence which encodes a complex obtained by the process of claim 5.

15. A process according to claim 1, characterized in that the immunogen is a hapten or an antigen.

16. A process according to claim 15 wherein said hapten is a peptide or a polysaccharide.

17. A complex which can be obtained by the process according to claim 1.

18. A nucleotide sequence which encodes a complex according to claim 17.

19. A nucleotide sequence according to claim 18, characterized in that it includes elements which enable expression of the complex to be targeted in a specific host cell.

20. A nucleotide sequence according to claim 18, characterized in that it is selected from the group consisting of DNA constructs and RNA constructs.

21. A vector, characterized in that it includes a nucleotide sequence according to claim 18.

22. A pharmaceutical composition that comprises a product which can be obtained by the process according claim 1, or a DNA vector according to claim 21 and a pharmaceutically acceptable carrier.

23. A vaccine that comprises a complex between an immunogen and a support molecule, which complex can be obtained by the process according to claim 1.

24. A vaccine according to claim 23 wherein said immunogen is derived from RSV surface glycoprotein G.

25. A process according to claim 1, characterized in that the support molecule is encoded by a sequence which is at least about 80% identical with SEQ ID NO: 74.

26. A process according to claim 1 wherein said immunogen is encoded by a sequence which is at least about 80% identical with the sequence encompassed between amino acids 130 and 230, inclusive, of the G protein of human RSV subgroups A or B.

27. A process according to claim 1 wherein said immunogen is encoded by a sequence which is at least about 80% identical with the sequence encompassed between amino acids 130 and 230, inclusive, of the G protein of bovine RSV subgroups A or B.

28. A process for improving the immunogenicity of an immunogen in vivo comprising the step of inserting or fusing DNA encoding an immunogen into DNA encoding a support whereby expression of the resulting DNA produces a complex, said complex comprising an immunogen covalently coupled to a support molecule, wherein said support molecule is a polypeptide fragment which binds specifically to mammalian serum albumin, and wherein said immunogen is derived from RSV surface glycoprotein: F and/or G.

29. A process according to claim 28, wherein said immunogen is encoded by the sequence encompassed between amino acids 130 and 230, inclusive, of the G protein of human RSV subgroups A or B, or of a sequence which is at least about 80% identical with said sequence encoding said G protein.

30. A process according to claim 29, characterized in that the proteins are derived from the G glycoprotein of RSV subgroups A and B that are genetically fused or chemically coupled to BB.

31. A process according to claim 28, wherein said immunogen is encoded by the sequence encompassed between amino acids 130 and 230, inclusive, of the G protein of bovine RSV subgroups A or B, or of a sequence which is at least about 80% identical with said sequence encoding said G protein.

32. A process according to claim 28, wherein said immunogen exhibits one of the sequences ID NO: 1 to ID NO: 73.

33. A process for improving the immunogenicity of an immunogen in vivo comprising the step of inserting or fusing DNA encoding an immunogen into DNA encoding a support whereby expression of the resulting DNA produces a complex, said complex comprising an immunogen covalently coupled to a support molecule, wherein said support molecule is a polypeptide fragment which binds specifically to mammalian serum albumin, and wherein said immunogen is derived from the surface protein of hepatitis virus A, B or C.

34. A process for improving the immunogenicity of an immunogen in vivo comprising the step of inserting or fusing DNA encoding an immunogen into DNA encoding a support whereby expression of the resulting DNA produces a complex, said complex comprising an immunogen covalently coupled to a support molecule, wherein said support molecule is a polypeptide fragment which binds specifically to mammalian serum albumin, and wherein said immunogen is a surface protein of the measles virus.

35. A process for improving the immunogenicity of an immunogen in vivo comprising the step of inserting or fusing DNA encoding an immunogen into DNA encoding a support whereby expression of the resulting DNA produces a complex, said complex comprising an immunogen covalently coupled to a support molecule, wherein said support molecule is a polypeptide fragment which binds specifically to mammalian serum albumin and wherein said immunogen is the surface protein of parainfluenza virus 3.

36. A process for improving the immunogenicity of an immunogen derived from RSV surface glycoprotein G comprising covalently coupling said immunogen to a support molecule to form a complex, wherein said support molecule is a polypeptide fragment which binds specifically to mammalian serum albumin.

37. A process according to claim 36 wherein said support molecule is encoded by the sequence as set forth in SEQ ID NO: 74 or a sequence which is at least about 80% identical with SEQ ID NO: 74.

38. A process according to claim 36 wherein said complex is formed by inserting or fusing DNA encoding said immunogen into DNA encoding said support whereby expression of the resulting DNA produces said complex.

39. A nucleotide sequence encoding the complex of claim 38.

40. A vector comprising the nucleotide sequence of claim 39.

41. A complex formed according to the process of claim 36.

42. A process according to claim 36 wherein said covalent coupling is effected chemically.

43. A process according to claim 42 wherein said immunogen is encoded by the sequence encompassed between amino acids 130 and 230, inclusive, of the G protein of human RSV subgroups A or B.

44. A process according to claim 42 wherein said immunogen is encoded by the sequence encompassed between amino acids 130 and 230, inclusive, of the G protein of bovine RSV subgroups A or B.

45. A process according to claim 42 wherein said immunogen exhibits one of the sequences ID NO: 1 to ID NO: 73.

46. A process according to claim 36, wherein said support molecule is encoded by a sequence which is at least about 80% identical with the sequence as set forth in SEQ ID NO: 74.

* * * * *

UNITED STATES PATENT AND TRADEMARK OFFICE
CERTIFICATE OF CORRECTION

PATENT NO.    : 6,149,911
DATED         : November 21, 2000
INVENTOR(S)   : Binz et al.

It is certified that error appears in the above-identified patent and that said Letters Patent is hereby corrected as shown below:

Column 3,
Line 13, please delete "23 (7.16%): Leu" and insert -- 25 (7.16%); Leu --
Line 24, please delete "Molecular weight: 39268" and insert -- Molecular weight 39288 --

Column 4,
Line 62, please delete "se(id No. 1" and insert -- seq id No. 1 --

Column 5,
Line 6, please delete "PVABB308" and insert -- pVABB308 -- and please delete "BBG2A and is" and insert -- BBG2A and --

Column 6,
Line 29, please delete "0.05°%" and insert -- 0.05% --

Column 10,
Line 26, please delete "log1$_{10}$" and insert -- log$_{10}$ --

Column 13,
Line 35, please delete "g of lung" and insert -- g of liver --

Column 14, table 7,
Line 5, please delete "TCID$_{50}$1/g" and insert -- TCID$_{50}$a/g --

Signed and Sealed this

Eighteenth Day of December, 2001

Attest:

JAMES E. ROGAN
*Attesting Officer*        *Director of the United States Patent and Trademark Office*

SEQUENCE LISTING (1) GENERAL INFORMATION:

(iii) NUMBER OF SEQUENCES: 78

(2) INFORMATION FOR SEQ ID NO: 1:

(i) SEQUENCE CHARACTERISTICS:
      (A) LENGTH: 303 base pairs
      (B) TYPE: nucleotide
      (C) STRANDEDNESS: single
      (D) TOPOLOGY: linear (ii) MOLECULE TYPE: cDNA (ix) FEATURE:
      (A) NAME/KEY: CDS
      (B) LOCATION:1..303

(xi) SEQUENCE DESCRIPTION: SEQ ID NO: 1:

```
ACC GTG AAA ACC AAA AAC ACC ACG ACC ACC CAG ACC CAG CCG AGC AAA        48
Thr Val Lys Thr Lys Asn Thr Thr Thr Thr Gln Thr Gln Pro Ser Lys
 1               5                  10                  15

CCG ACC ACC AAA CAG CGT CAG AAC AAA CCG CCG AAC AAA CCG AAC AAC        96
Pro Thr Thr Lys Gln Arg Gln Asn Lys Pro Pro Asn Lys Pro Asn Asn
                20                  25                  30
```

-continued

```
GAT TTC CAT TTC GAA GTG TTC AAC TTC GTG CCG TGC AGC ATC TGC AGC      144
Asp Phe His Phe Glu Val Phe Asn Phe Val Pro Cys Ser Ile Cys Ser
         35                  40                  45

AAC AAC CCG ACC TGC TGG GCG ATC TGC AAA CGT ATC CCG AAC AAA AAA      192
Asn Asn Pro Thr Cys Trp Ala Ile Cys Lys Arg Ile Pro Asn Lys Lys
 50                  55                  60

CCG GGC AAA AAA ACC ACG ACC AAA CCG ACC AAA AAA CCG ACC TTC AAA      240
Pro Gly Lys Lys Thr Thr Thr Lys Pro Thr Lys Lys Pro Thr Phe Lys
 65                  70                  75                  80

ACC ACC AAA AAA GAT CAT AAA CCG CAG ACC ACC AAA CCG AAA GAA GTG      288
Thr Thr Lys Lys Asp His Lys Pro Gln Thr Thr Lys Pro Lys Glu Val
                 85                  90                  95

CCG ACC ACC AAA CCG                                                  303
Pro Thr Thr Lys Pro
            100
```

(2) INFORMATION FOR SEQ ID NO: 2:

(i) SEQUENCE CHARACTERISTICS:
        (A) LENGTH: 303 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..303

(xi) SEQUENCE DESCRIPTION: SEQ ID NO: 2:

```
ACC GCG CAG ACC AAA GGC CGT ATC ACC ACC AGC ACC CAG ACC AAC AAA       48
Thr Ala Gln Thr Lys Gly Arg Ile Thr Thr Ser Thr Gln Thr Asn Lys
 1                   5                  10                  15

CCG AGC ACC AAA AGC CGT AGC AAA AAC CCG CCG AAA AAA CCG AAA GAT       96
Pro Ser Thr Lys Ser Arg Ser Lys Asn Pro Pro Lys Lys Pro Lys Asp
                 20                  25                  30

GAT TAC CAC TTC GAA GTG TTC AAC TTC GTG CCC TGC AGC ATC TGC GGC      144
Asp Tyr His Phe Glu Val Phe Asn Phe Val Pro Cys Ser Ile Cys Gly
         35                  40                  45

AAC AAC CAG CTG TGC AAA AGC ATC TGC AAA ACC ATC CCG AGC AAC AAA      192
Asn Asn Gln Leu Cys Lys Ser Ile Cys Lys Thr Ile Pro Ser Asn Lys
 50                  55                  60

CCG AAA AAG AAA CCG ACC ATC AAA CCG ACC AAC AAA CCG ACC ACC AAA      240
Pro Lys Lys Lys Pro Thr Ile Lys Pro Thr Asn Lys Pro Thr Thr Lys
 65                  70                  75                  80

ACC ACC AAC AAA CGT GAT CCG AAA ACC CCG GCG AAA ATG CCG AAG AAG      288
Thr Thr Asn Lys Arg Asp Pro Lys Thr Pro Ala Lys Met Pro Lys Lys
                 85                  90                  95

GAA ATC ATC ACC AAC                                                  303
Glu Ile Ile Thr Asn
            100
```

(2) INFORMATION FOR SEQ ID NO: 3:

(i) SEQUENCE CHARACTERISTICS:
        (A) LENGTH: 303 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS -continued (B) LOCATION:1..303

(xi) SEQUENCE DESCRIPTION: SEQ ID NO: 3:

```
ACC GTG AAA ACC AAA AAC ACC ACG ACC ACC CAG ACC CAG CCG AGC AAA      48
Thr Val Lys Thr Lys Asn Thr Thr Thr Thr Gln Thr Gln Pro Ser Lys
 1               5                  10                  15

CCG ACC ACC AAA CAG CGT CAG AAC AAA CCG CCG AAC AAA CCG AAC AAC      96
Pro Thr Thr Lys Gln Arg Gln Asn Lys Pro Pro Asn Lys Pro Asn Asn
             20                  25                  30

GAT TTC CAT TTC GAA GTG TTC AAC TTC GTG CCG AGC AGC ATC TGC AGC     144
Asp Phe His Phe Glu Val Phe Asn Phe Val Pro Ser Ser Ile Cys Ser
                 35                  40                  45

AAC AAC CCG ACC TGC TGG GCG ATC AGC AAA CGT ATC CCG AAC AAA AAA     192
Asn Asn Pro Thr Cys Trp Ala Ile Ser Lys Arg Ile Pro Asn Lys Lys
         50                  55                  60

CCG GGC AAA AAA ACC ACG ACC AAA CCG ACC AAA AAA CCG ACC TTC AAA     240
Pro Gly Lys Lys Thr Thr Thr Lys Pro Thr Lys Lys Pro Thr Phe Lys
 65                  70                  75                  80

ACC ACC AAA AAA GAT CAT AAA CCG CAG ACC ACC AAA CCG AAA GAA GTG     288
Thr Thr Lys Lys Asp His Lys Pro Gln Thr Thr Lys Pro Lys Glu Val
                 85                  90                  95

CCG ACC ACC AAA CCG                                                 303
Pro Thr Thr Lys Pro
            100
```

(2) INFORMATION FOR SEQ ID NO: 4:

(i) SEQUENCE CHARACTERISTICS:
        (A) LENGTH: 303 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..303

(xi) SEQUENCE DESCRIPTION: SEQ ID NO: 4:

```
ACC GCG CAG ACC AAA GGC CGT ATC ACC ACC AGC ACC CAG ACC AAC AAA      48
Thr Ala Gln Thr Lys Gly Arg Ile Thr Thr Ser Thr Gln Thr Asn Lys
 1               5                  10                  15

CCG AGC ACC AAA AGC CGT AGC AAA AAC CCG CCG AAA AAA CCG AAA GAT      96
Pro Ser Thr Lys Ser Arg Ser Lys Asn Pro Pro Lys Lys Pro Lys Asp
             20                  25                  30

GAT TAC CAC TTC GAA GTG TTC AAC TTC GTG CCC AGC AGC ATC TGC GGC     144
Asp Tyr His Phe Glu Val Phe Asn Phe Val Pro Ser Ser Ile Cys Gly
                 35                  40                  45

AAC AAC CAG CTG TGC AAA AGC ATC AGC AAA ACC ATC CCG AGC AAC AAA     192
Asn Asn Gln Leu Cys Lys Ser Ile Ser Lys Thr Ile Pro Ser Asn Lys
         50                  55                  60

CCG AAA AAG AAA CCG ACC ATC AAA CCG ACC AAC AAA CCG ACC ACC AAA     240
Pro Lys Lys Lys Pro Thr Ile Lys Pro Thr Asn Lys Pro Thr Thr Lys
 65                  70                  75                  80

ACC ACC AAC AAA CGT GAT CCG AAA ACC CCG GCG AAA ATG CCG AAG AAG     288
Thr Thr Asn Lys Arg Asp Pro Lys Thr Pro Ala Lys Met Pro Lys Lys
                 85                  90                  95

GAA ATC ATC ACC AAC                                                 303
Glu Ile Ile Thr Asn
            100
```

(2) INFORMATION FOR SEQ ID NO: 5:

```
    (i) SEQUENCE CHARACTERISTICS:
        (A) LENGTH: 42 base pairs
        (B) TYPE: nucleotide
        (C) STRANDEDNESS: single
        (D) TOPOLOGY: linear (ii) MOLECULE TYPE:  cDNA (ix) FEATURE:
        (A) NAME/KEY: CDS
        (B) LOCATION:1..42

(xi) SEQUENCE DESCRIPTION: SEQ ID NO: 5:

AGC ATC TGC AGC AAC AAC CCG ACC TGC TGG GCG ATC TGC AAA            42
Ser Ile Cys Ser Asn Asn Pro Thr Cys Trp Ala Ile Cys Lys
  1               5                  10

(2) INFORMATION FOR SEQ ID NO: 6:

(i) SEQUENCE CHARACTERISTICS:
        (A) LENGTH: 42 base pairs
        (B) TYPE: nucleotide
        (C) STRANDEDNESS: single
        (D) TOPOLOGY: linear (ii) MOLECULE TYPE:  cDNA (ix) FEATURE:
        (A) NAME/KEY: CDS
        (B) LOCATION:1..42

(xi) SEQUENCE DESCRIPTION: SEQ ID NO: 6:

AGC ATC TGC GGC AAC AAC CAG CTG TGC AAA AGC ATC TGC AAA            42
Ser Ile Cys Gly Asn Asn Gln Leu Cys Lys Ser Ile Cys Lys
  1               5                  10

(2) INFORMATION FOR SEQ ID NO: 7:

(i) SEQUENCE CHARACTERISTICS:
        (A) LENGTH: 42 base pairs
        (B) TYPE: nucleotide
        (C) STRANDEDNESS: single
        (D) TOPOLOGY: linear (ii) MOLECULE TYPE:  cDNA (ix) FEATURE:
        (A) NAME/KEY: CDS
        (B) LOCATION:1..42

(xi) SEQUENCE DESCRIPTION: SEQ ID NO: 7:

AGC ATC TGC AGC AAC AAC CCG ACC TGC TGG GCG ATC AGC AAA            42
Ser Ile Cys Ser Asn Asn Pro Thr Cys Trp Ala Ile Ser Lys
  1               5                  10

(2) INFORMATION FOR SEQ ID NO: 8:

(i) SEQUENCE CHARACTERISTICS:
        (A) LENGTH: 42 base pairs
        (B) TYPE: nucleotide
        (C) STRANDEDNESS: single
        (D) TOPOLOGY: linear (ii) MOLECULE TYPE:  cDNA (ix) FEATURE:
        (A) NAME/KEY: CDS
        (B) LOCATION:1..42

(xi) SEQUENCE DESCRIPTION: SEQ ID NO: 8:

AGC ATC TGC GGC AAC AAC CAG CTG TGC AAA AGC ATC AGC AAA            42
```

```
Ser Ile Cys Gly Asn Asn Gln Leu Cys Lys Ser Ile Ser Lys
1               5                   10
```

(2) INFORMATION FOR SEQ ID NO: 9:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: Peptide (ix) FEATURE:
        (A) NAME/KEY: Modified-site
        (B) LOCATION:9
        (D) OTHER INFORMATION:/Xaa means Orn (xi) SEQUENCE DESCRIPTION: SEQ ID NO: 9:

```
Ser Ile Asp Ser Asn Asn Pro Thr Xaa Trp Ala Ile Cys Lys
1               5                   10
```

(2) INFORMATION FOR SEQ ID NO: 10:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: Peptide (ix) FEATURE:
        (A) NAME/KEY: Modified-site
        (B) LOCATION:9
        (D) OTHER INFORMATION:/Xaa means Orn (xi) SEQUENCE DESCRIPTION: SEQ ID NO: 10:

```
Ser Ile Asp Gly Asn Asn Gln Leu Xaa Lys Ser Ile Cys Lys
1               5                   10
```

(2) INFORMATION FOR SEQ ID NO: 11:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: Peptide (ix) FEATURE:
        (A) NAME/KEY: Modified-site
        (B) LOCATION:9
        (D) OTHER INFORMATION:/Xaa means Orn (xi) SEQUENCE DESCRIPTION: SEQ ID NO: 11:

```
Ser Ile Asp Ser Asn Asn Pro Thr Xaa Trp Ala Ile Ser Lys
1               5                   10
```

(2) INFORMATION FOR SEQ ID NO: 12:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: Peptide (ix) FEATURE:
        (A) NAME/KEY: Modified-site (B) LOCATION:9
                (D) OTHER INFORMATION:/Xaa means Orn (xi) SEQUENCE DESCRIPTION: SEQ ID NO: 12:

Ser Ile Asp Gly Asn Asn Gln Leu Xaa Lys Ser Ile Ser Lys
1               5                   10

(2) INFORMATION FOR SEQ ID NO: 13:

(i) SEQUENCE CHARACTERISTICS:
                (A) LENGTH: 48 base pairs
                (B) TYPE: nucleotide
                (C) STRANDEDNESS: single
                (D) TOPOLOGY: linear (ii) MOLECULE TYPE:  cDNA (ix) FEATURE:
                (A) NAME/KEY: CDS
                (B) LOCATION:1..48

(xi) SEQUENCE DESCRIPTION: SEQ ID NO: 13:

AGC AAA CCG ACC ACC AAA CAG CGT CAG AAC AAA CCG CCG AAC AAA CCG      48
Ser Lys Pro Thr Thr Lys Gln Arg Gln Asn Lys Pro Pro Asn Lys Pro
1               5                   10                  15

(2) INFORMATION FOR SEQ ID NO: 14:

(i) SEQUENCE CHARACTERISTICS:
                (A) LENGTH: 303 base pairs
                (B) TYPE: nucleotide
                (C) STRANDEDNESS: single
                (D) TOPOLOGY: linear (ii) MOLECULE TYPE:  cDNA (ix) FEATURE:
                (A) NAME/KEY: CDS
                (B) LOCATION:1..303

(xi) SEQUENCE DESCRIPTION: SEQ ID NO: 14:

ACC GTG AAA ACC AAA AAC ACC ACG ACC ACC CAG ACC CAG CCG AGC AAA      48
Thr Val Lys Thr Lys Asn Thr Thr Thr Thr Gln Thr Gln Pro Ser Lys
1               5                   10                  15

CCG ACC ACC AAA CAG CGT CAG AAC AAA CCG CCG AAC AAA CCG AAC AAC      96
Pro Thr Thr Lys Gln Arg Gln Asn Lys Pro Pro Asn Lys Pro Asn Asn
                20                  25                  30

GAT TCC CAT TCC GAA GTG TCC AAC TCC GTG CCG AGC AGC ATC TGC AGC     144
Asp Ser His Ser Glu Val Ser Asn Ser Val Pro Ser Ser Ile Cys Ser
            35                  40                  45

AAC AAC CCG ACC TGC TGG GCG ATC AGC AAA CGT ATC CCG AAC AAA AAA     192
Asn Asn Pro Thr Cys Trp Ala Ile Ser Lys Arg Ile Pro Asn Lys Lys
        50                  55                  60

CCG GGC AAA AAA ACC ACG ACC AAA CCG ACC AAA AAA CCG ACC TTC AAA     240
Pro Gly Lys Lys Thr Thr Thr Lys Pro Thr Lys Lys Pro Thr Phe Lys
65              70                  75                  80

ACC ACC AAA AAA GAT CAT AAA CCG CAG ACC ACC AAA CCG AAA GAA GTG     288
Thr Thr Lys Lys Asp His Lys Pro Gln Thr Thr Lys Pro Lys Glu Val
                85                  90                  95

CCG ACC ACC AAA CCG                                                 303
Pro Thr Thr Lys Pro
            100

(2) INFORMATION FOR SEQ ID NO: 15:

(i) SEQUENCE CHARACTERISTICS:
                (A) LENGTH: 51 base pairs

-continued (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..51

(xi) SEQUENCE DESCRIPTION: SEQ ID NO: 15:

```
GTG CCG TGC AGC ATC TGC AGC AAC AAC CCG ACC TGC TGG GCC ATC TGC      48
Val Pro Cys Ser Ile Cys Ser Asn Asn Pro Thr Cys Trp Ala Ile Cys
 1               5                  10                  15

AAA                                                                  51
Lys
```

(2) INFORMATION FOR SEQ ID NO: 16:

(i) SEQUENCE CHARACTERISTICS:
        (A) LENGTH: 51 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..51

(xi) SEQUENCE DESCRIPTION: SEQ ID NO: 16:

```
GTG CCG AGC AGC ATC TGC AGC AAC AAC CCG ACC TGC TGG GCG ATC AGC      48
Val Pro Ser Ser Ile Cys Ser Asn Asn Pro Thr Cys Trp Ala Ile Ser
 1               5                  10                  15

AAA                                                                  51
Lys
```

(2) INFORMATION FOR SEQ ID NO: 17:

(i) SEQUENCE CHARACTERISTICS:
        (A) LENGTH: 51 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..51

(xi) SEQUENCE DESCRIPTION: SEQ ID NO: 17:

```
GTG CCC TGC AGC ATC TGC GGC AAC AAC CAG CTG TGC AAA AGC ATC TGC      48
Val Pro Cys Ser Ile Cys Gly Asn Asn Gln Leu Cys Lys Ser Ile Cys
 1               5                  10                  15

AAA                                                                  51
Lys
```

(2) INFORMATION FOR SEQ ID NO: 18:

(i) SEQUENCE CHARACTERISTICS:
        (A) LENGTH: 51 base pairs
        (B) TYPE: nucleotide
        (C) STRANDEDNESS: single
        (D) TOPOLOGY: linear (ii) MOLECULE TYPE: cDNA (ix) FEATURE:

(A) NAME/KEY: CDS
                (B) LOCATION:1..51

(xi) SEQUENCE DESCRIPTION: SEQ ID NO: 18:

GTG CCC AGC AGC ATC TGC GGC AAC AAC CAG CTG TGC AAA AGC ATC AGC         48
Val Pro Ser Ser Ile Cys Gly Asn Asn Gln Leu Cys Lys Ser Ile Ser
 1               5                  10                  15

AAA                                                                     51
Lys (2) INFORMATION FOR SEQ ID NO: 19:

(i) SEQUENCE CHARACTERISTICS:
                (A) LENGTH: 17 amino acids
                (B) TYPE: amino acid
                (C) STRANDEDNESS: single
                (D) TOPOLOGY: linear (ii) MOLECULE TYPE: Peptide (ix) FEATURE:
                (A) NAME/KEY: Modified-site
                (B) LOCATION:12
                (D) OTHER INFORMATION:/Xaa means Orn (ix) FEATURE:
                (A) NAME/KEY: Modified-site
                (B) LOCATION:16
                (D) OTHER INFORMATION:/Xaa means Orn (xi) SEQUENCE DESCRIPTION: SEQ ID NO: 19:

Val Pro Asp Ser Ile Asp Ser Asn Asn Pro Thr Xaa Trp Ala Ile Xaa
 1               5                  10                  15

Lys (2) INFORMATION FOR SEQ ID NO: 20:

(i) SEQUENCE CHARACTERISTICS:
                (A) LENGTH: 17 amino acids
                (B) TYPE: amino acid
                (C) STRANDEDNESS: single
                (D) TOPOLOGY: linear (ii) MOLECULE TYPE: Peptide (ix) FEATURE:
                (A) NAME/KEY: Modified-site
                (B) LOCATION:12
                (D) OTHER INFORMATION:/Xaa means Orn (xi) SEQUENCE DESCRIPTION: SEQ ID NO: 20:

Val Pro Ser Ser Ile Asp Ser Asn Asn Pro Thr Xaa Trp Ala Ile Ser
 1               5                  10                  15

Lys (2) INFORMATION FOR SEQ ID NO: 21:

(i) SEQUENCE CHARACTERISTICS:
                (A) LENGTH: 17 amino acids
                (B) TYPE: amino acid
                (C) STRANDEDNESS: single
                (D) TOPOLOGY: linear (ii) MOLECULE TYPE: Peptide (ix) FEATURE:
                (A) NAME/KEY: Modified-site
                (B) LOCATION:12
                (D) OTHER INFORMATION:/Xaa means Orn

```
    (ix) FEATURE:
          (A) NAME/KEY: Modified-site
          (B) LOCATION:16
          (D) OTHER INFORMATION:/Xaa means Orn (xi) SEQUENCE DESCRIPTION: SEQ ID NO: 21:

Val Pro Asp Ser Ile Asp Gly Asn Asn Gln Leu Xaa Lys Ser Ile Xaa
1               5                   10                  15

Lys (2) INFORMATION FOR SEQ ID NO: 22:

(i) SEQUENCE CHARACTERISTICS:
         (A) LENGTH: 17 amino acids
         (B) TYPE: amino acid
         (C) STRANDEDNESS: single
         (D) TOPOLOGY: linear (ii) MOLECULE TYPE: Peptide (ix) FEATURE:
          (A) NAME/KEY: Modified-site
          (B) LOCATION:12
          (D) OTHER INFORMATION:/Xaa means Orn (xi) SEQUENCE DESCRIPTION: SEQ ID NO: 22:

Val Pro Ser Ser Ile Asp Gly Asn Asn Gln Leu Xaa Lys Ser Ile Ser
1               5                   10                  15

Lys (2) INFORMATION FOR SEQ ID NO: 23:

(i) SEQUENCE CHARACTERISTICS:
         (A) LENGTH: 183 base pairs
         (B) TYPE: nucleotide
         (C) STRANDEDNESS: single
         (D) TOPOLOGY: linear (ii) MOLECULE TYPE:  cDNA (ix) FEATURE:
          (A) NAME/KEY: CDS
          (B) LOCATION:1..183

(xi) SEQUENCE DESCRIPTION: SEQ ID NO: 23:

CAG ACC CAG CCG AGC AAA CCG ACC ACC AAA CAG CGT CAG AAC AAA CCG        48
Gln Thr Gln Pro Ser Lys Pro Thr Thr Lys Gln Arg Gln Asn Lys Pro
 1               5                   10                  15

CCG AAC AAA CCG AAC AAC GAT TTC CAT TTC GAA GTG TTC AAC TTC GTG        96
Pro Asn Lys Pro Asn Asn Asp Phe His Phe Glu Val Phe Asn Phe Val
                20                  25                  30

CCG TGC AGC ATC TGC AGC AAC AAC CCG ACC TGC TGG GCG ATC TGC AAA       144
Pro Cys Ser Ile Cys Ser Asn Asn Pro Thr Cys Trp Ala Ile Cys Lys
            35                  40                  45

CGT ATC CCG AAC AAA AAA CCG GGC AAA AAA ACC ACG ACC                   183
Arg Ile Pro Asn Lys Lys Pro Gly Lys Lys Thr Thr Thr
        50                  55                  60

(2) INFORMATION FOR SEQ ID NO: 24:

(i) SEQUENCE CHARACTERISTICS:
         (A) LENGTH: 177 base pairs
         (B) TYPE: nucleotide
         (C) STRANDEDNESS: single
         (D) TOPOLOGY: linear (ii) MOLECULE TYPE:  cDNA
```

```
            (ix) FEATURE:
                  (A) NAME/KEY: CDS
                  (B) LOCATION:1..177

(xi) SEQUENCE DESCRIPTION: SEQ ID NO: 24:

CAG ACC CAG CCG AGC AAA CCG ACC ACC AAA CAG CGT CAG AAC AAA CCG        48
Gln Thr Gln Pro Ser Lys Pro Thr Thr Lys Gln Arg Gln Asn Lys Pro
  1               5                  10                  15

CCG AAC AAA CCG AAC AAC GAT TTC CAT TTC GAA GTG TTC AAC TTC GTG        96
Pro Asn Lys Pro Asn Asn Asp Phe His Phe Glu Val Phe Asn Phe Val
                 20                  25                  30

CCG TGC AGC ATC TGC AGC AAC AAC CCG ACC TGC TGG GCG ATC TGC AAA       144
Pro Cys Ser Ile Cys Ser Asn Asn Pro Thr Cys Trp Ala Ile Cys Lys
             35                  40                  45

CGT ATC CCG AAC AAA AAA CCG GGC AAA AAA ACC                           177
Arg Ile Pro Asn Lys Lys Pro Gly Lys Lys Thr
         50                  55

(2) INFORMATION FOR SEQ ID NO: 25:

(i) SEQUENCE CHARACTERISTICS:
                  (A) LENGTH: 171 base pairs
                  (B) TYPE: nucleotide
                  (C) STRANDEDNESS: single
                  (D) TOPOLOGY: linear (ii) MOLECULE TYPE:  cDNA (ix) FEATURE:
                  (A) NAME/KEY: CDS
                  (B) LOCATION:1..171

(xi) SEQUENCE DESCRIPTION: SEQ ID NO: 25:

CAG ACC CAG CCG AGC AAA CCG ACC ACC AAA CAG CGT CAG AAC AAA CCG        48
Gln Thr Gln Pro Ser Lys Pro Thr Thr Lys Gln Arg Gln Asn Lys Pro
  1               5                  10                  15

CCG AAC AAA CCG AAC AAC GAT TTC CAT TTC GAA GTG TTC AAC TTC GTG        96
Pro Asn Lys Pro Asn Asn Asp Phe His Phe Glu Val Phe Asn Phe Val
                 20                  25                  30

CCG TGC AGC ATC TGC AGC AAC AAC CCG ACC TGC TGG GCG ATC TGC AAA       144
Pro Cys Ser Ile Cys Ser Asn Asn Pro Thr Cys Trp Ala Ile Cys Lys
             35                  40                  45

CGT ATC CCG AAC AAA AAA CCG GGC AAA                                   171
Arg Ile Pro Asn Lys Lys Pro Gly Lys
         50                  55

(2) INFORMATION FOR SEQ ID NO: 26:

(i) SEQUENCE CHARACTERISTICS:
                  (A) LENGTH: 165 base pairs
                  (B) TYPE: nucleotide
                  (C) STRANDEDNESS: single
                  (D) TOPOLOGY: linear (ii) MOLECULE TYPE:  cDNA (ix) FEATURE:
                  (A) NAME/KEY: CDS
                  (B) LOCATION:1..165

(xi) SEQUENCE DESCRIPTION: SEQ ID NO: 26:

CAG ACC CAG CCG AGC AAA CCG ACC ACC AAA CAG CGT CAG AAC AAA CCG        48
Gln Thr Gln Pro Ser Lys Pro Thr Thr Lys Gln Arg Gln Asn Lys Pro
  1               5                  10                  15

CCG AAC AAA CCG AAC AAC GAT TTC CAT TTC GAA GTG TTC AAC TTC GTG        96
Pro Asn Lys Pro Asn Asn Asp Phe His Phe Glu Val Phe Asn Phe Val
                 20                  25                  30
```

```
CCG TGC AGC ATC TGC AGC AAC AAC CCG ACC TGC TGG GCG ATC TGC AAA     144
Pro Cys Ser Ile Cys Ser Asn Asn Pro Thr Cys Trp Ala Ile Cys Lys
        35                  40                  45

CGT ATC CCG AAC AAA AAA CCG                                          165
Arg Ile Pro Asn Lys Lys Pro
 50                  55
```

(2) INFORMATION FOR SEQ ID NO: 27:

(i) SEQUENCE CHARACTERISTICS:
        (A) LENGTH: 159 base pairs
        (B) TYPE: nucleotide
        (C) STRANDEDNESS: single
        (D) TOPOLOGY: linear (ii) MOLECULE TYPE:  cDNA (ix) FEATURE:
        (A) NAME/KEY: CDS
        (B) LOCATION:1..159

(xi) SEQUENCE DESCRIPTION: SEQ ID NO: 27:

```
CAG ACC CAG CCG AGC AAA CCG ACC ACC AAA CAG CGT CAG AAC AAA CCG      48
Gln Thr Gln Pro Ser Lys Pro Thr Thr Lys Gln Arg Gln Asn Lys Pro
 1               5                  10                  15

CCG AAC AAA CCG AAC AAC GAT TTC CAT TTC GAA GTG TTC AAC TTC GTG      96
Pro Asn Lys Pro Asn Asn Asp Phe His Phe Glu Val Phe Asn Phe Val
                20                  25                  30

CCG TGC AGC ATC TGC AGC AAC AAC CCG ACC TGC TGG GCG ATC TGC AAA     144
Pro Cys Ser Ile Cys Ser Asn Asn Pro Thr Cys Trp Ala Ile Cys Lys
        35                  40                  45

CGT ATC CCG AAC AAA                                                  159
Arg Ile Pro Asn Lys
 50
```

(2) INFORMATION FOR SEQ ID NO: 28:

(i) SEQUENCE CHARACTERISTICS:
        (A) LENGTH: 153 base pairs
        (B) TYPE: nucleotide
        (C) STRANDEDNESS: single
        (D) TOPOLOGY: linear (ii) MOLECULE TYPE:  cDNA (ix) FEATURE:
        (A) NAME/KEY: CDS
        (B) LOCATION:1..153

(xi) SEQUENCE DESCRIPTION: SEQ ID NO: 28:

```
CAG ACC CAG CCG AGC AAA CCG ACC ACC AAA CAG CGT CAG AAC AAA CCG      48
Gln Thr Gln Pro Ser Lys Pro Thr Thr Lys Gln Arg Gln Asn Lys Pro
 1               5                  10                  15

CCG AAC AAA CCG AAC AAC GAT TTC CAT TTC GAA GTG TTC AAC TTC GTG      96
Pro Asn Lys Pro Asn Asn Asp Phe His Phe Glu Val Phe Asn Phe Val
                20                  25                  30

CCG TGC AGC ATC TGC AGC AAC AAC CCG ACC TGC TGG GCG ATC TGC AAA     144
Pro Cys Ser Ile Cys Ser Asn Asn Pro Thr Cys Trp Ala Ile Cys Lys
        35                  40                  45

CGT ATC CCG                                                          153
Arg Ile Pro
 50
```

(2) INFORMATION FOR SEQ ID NO: 29:

(i) SEQUENCE CHARACTERISTICS:

(A) LENGTH: 99 base pairs
            (B) TYPE: nucleotide
            (C) STRANDEDNESS: single
            (D) TOPOLOGY: linear (ii) MOLECULE TYPE: cDNA (ix) FEATURE:
            (A) NAME/KEY: CDS
            (B) LOCATION:1..99

(xi) SEQUENCE DESCRIPTION: SEQ ID NO: 29:

```
AAA CCG AAC AAC GAT TTC CAT TTC GAA GTG TTC AAC TTC GTG CCG TGC      48
Lys Pro Asn Asn Asp Phe His Phe Glu Val Phe Asn Phe Val Pro Cys
 1               5                  10                  15

AGC ATC TGC AGC AAC AAC CCG ACC TGC TGG GCG ATC TGC AAA CGT ATC      96
Ser Ile Cys Ser Asn Asn Pro Thr Cys Trp Ala Ile Cys Lys Arg Ile
            20                  25                  30

CCG                                                                  99
Pro
```

(2) INFORMATION FOR SEQ ID NO: 30:

(i) SEQUENCE CHARACTERISTICS:
            (A) LENGTH: 183 base pairs
            (B) TYPE: nucleotide
            (C) STRANDEDNESS: single
            (D) TOPOLOGY: linear (ii) MOLECULE TYPE: cDNA (ix) FEATURE:
            (A) NAME/KEY: CDS
            (B) LOCATION:1..183

(xi) SEQUENCE DESCRIPTION: SEQ ID NO: 30:

```
CAG ACC CAG CCG AGC AAA CCG ACC ACC AAA CAG CGT CAG AAC AAA CCG      48
Gln Thr Gln Pro Ser Lys Pro Thr Thr Lys Gln Arg Gln Asn Lys Pro
 1               5                  10                  15

CCG AAC AAA CCG AAC AAC GAT TTC CAT TTC GAA GTG TTC AAC TTC GTG      96
Pro Asn Lys Pro Asn Asn Asp Phe His Phe Glu Val Phe Asn Phe Val
            20                  25                  30

CCG AGC AGC ATC TGC AGC AAC AAC CCG ACC TGC TGG GCG ATC AGC AAA     144
Pro Ser Ser Ile Cys Ser Asn Asn Pro Thr Cys Trp Ala Ile Ser Lys
        35                  40                  45

CGT ATC CCG AAC AAA AAA CCG GGC AAA AAA ACC ACG ACC                 183
Arg Ile Pro Asn Lys Lys Pro Gly Lys Lys Thr Thr Thr
 50                  55                  60
```

(2) INFORMATION FOR SEQ ID NO: 31:

(i) SEQUENCE CHARACTERISTICS:
            (A) LENGTH: 177 base pairs
            (B) TYPE: nucleotide
            (C) STRANDEDNESS: single
            (D) TOPOLOGY: linear (ii) MOLECULE TYPE: cDNA (ix) FEATURE:
            (A) NAME/KEY: CDS
            (B) LOCATION:1..177

(xi) SEQUENCE DESCRIPTION: SEQ ID NO: 31:

```
CAG ACC CAG CCG AGC AAA CCG ACC ACC AAA CAG CGT CAG AAC AAA CCG      48
Gln Thr Gln Pro Ser Lys Pro Thr Thr Lys Gln Arg Gln Asn Lys Pro
 1               5                  10                  15

CCG AAC AAA CCG AAC AAC GAT TTC CAT TTC GAA GTG TTC AAC TTC GTG      96
```

```
Pro Asn Lys Pro Asn Asn Asp Phe His Phe Glu Val Phe Asn Phe Val
         20                  25                  30

CCG AGC AGC ATC TGC AGC AAC AAC CCG ACC TGC TGG GCG ATC AGC AAA        144
Pro Ser Ser Ile Cys Ser Asn Asn Pro Thr Cys Trp Ala Ile Ser Lys
         35                  40                  45

CGT ATC CCG AAC AAA AAA CCG GGC AAA AAA ACC                            177
Arg Ile Pro Asn Lys Lys Pro Gly Lys Lys Thr
 50              55
```

(2) INFORMATION FOR SEQ ID NO: 32:

(i) SEQUENCE CHARACTERISTICS:
        (A) LENGTH: 171 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..171

(xi) SEQUENCE DESCRIPTION: SEQ ID NO: 32:

```
CAG ACC CAG CCG AGC AAA CCG ACC ACC AAA CAG CGT CAG AAC AAA CCG         48
Gln Thr Gln Pro Ser Lys Pro Thr Thr Lys Gln Arg Gln Asn Lys Pro
 1               5                  10                  15

CCG AAC AAA CCG AAC AAC GAT TTC CAT TTC GAA GTG TTC AAC TTC GTG         96
Pro Asn Lys Pro Asn Asn Asp Phe His Phe Glu Val Phe Asn Phe Val
         20                  25                  30

CCG AGC AGC ATC TGC AGC AAC AAC CCG ACC TGC TGG GCG ATC AGC AAA        144
Pro Ser Ser Ile Cys Ser Asn Asn Pro Thr Cys Trp Ala Ile Ser Lys
         35                  40                  45

CGT ATC CCG AAC AAA AAA CCG GGC AAA                                    171
Arg Ile Pro Asn Lys Lys Pro Gly Lys
 50              55
```

(2) INFORMATION FOR SEQ ID NO: 33:

(i) SEQUENCE CHARACTERISTICS:
        (A) LENGTH: 165 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..165

(xi) SEQUENCE DESCRIPTION: SEQ ID NO: 33:

```
CAG ACC CAG CCG AGC AAA CCG ACC ACC AAA CAG CGT CAG AAC AAA CCG         48
Gln Thr Gln Pro Ser Lys Pro Thr Thr Lys Gln Arg Gln Asn Lys Pro
 1               5                  10                  15

CCG AAC AAA CCG AAC AAC GAT TTC CAT TTC GAA GTG TTC AAC TTC GTG         96
Pro Asn Lys Pro Asn Asn Asp Phe His Phe Glu Val Phe Asn Phe Val
         20                  25                  30

CCG AGC AGC ATC TGC AGC AAC AAC CCG ACC TGC TGG GCG ATC AGC AAA        144
Pro Ser Ser Ile Cys Ser Asn Asn Pro Thr Cys Trp Ala Ile Ser Lys
         35                  40                  45

CGT ATC CCG AAC AAA AAA CCG                                            165
Arg Ile Pro Asn Lys Lys Pro
 50              55
```

(2) INFORMATION FOR SEQ ID NO: 34:

(i) SEQUENCE CHARACTERISTICS:
    (A) LENGTH: 159 base pairs
    (B) TYPE: nucleotide
    (C) STRANDEDNESS: single
    (D) TOPOLOGY: linear (ii) MOLECULE TYPE: cDNA (ix) FEATURE:
    (A) NAME/KEY: CDS
    (B) LOCATION:1..159

(xi) SEQUENCE DESCRIPTION: SEQ ID NO: 34:

```
CAG ACC CAG CCG AGC AAA CCG ACC ACC AAA CAG CGT CAG AAC AAA CCG      48
Gln Thr Gln Pro Ser Lys Pro Thr Thr Lys Gln Arg Gln Asn Lys Pro
 1               5                  10                  15

CCG AAC AAA CCG AAC AAC GAT TTC CAT TTC GAA GTG TTC AAC TTC GTG      96
Pro Asn Lys Pro Asn Asn Asp Phe His Phe Glu Val Phe Asn Phe Val
                20                  25                  30

CCG AGC AGC ATC TGC AGC AAC AAC CCG ACC TGC TGG GCG ATC AGC AAA     144
Pro Ser Ser Ile Cys Ser Asn Asn Pro Thr Cys Trp Ala Ile Ser Lys
            35                  40                  45

CGT ATC CCG AAC AAA                                                 159
Arg Ile Pro Asn Lys
    50
```

(2) INFORMATION FOR SEQ ID NO: 35:

(i) SEQUENCE CHARACTERISTICS:
        (A) LENGTH: 153 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..153

(xi) SEQUENCE DESCRIPTION: SEQ ID NO: 35:

```
CAG ACC CAG CCG AGC AAA CCG ACC ACC AAA CAG CGT CAG AAC AAA CCG      48
Gln Thr Gln Pro Ser Lys Pro Thr Thr Lys Gln Arg Gln Asn Lys Pro
 1               5                  10                  15

CCG AAC AAA CCG AAC AAC GAT TTC CAT TTC GAA GTG TTC AAC TTC GTG      96
Pro Asn Lys Pro Asn Asn Asp Phe His Phe Glu Val Phe Asn Phe Val
                20                  25                  30

CCG AGC AGC ATC TGC AGC AAC AAC CCG ACC TGC TGG GCG ATC AGC AAA     144
Pro Ser Ser Ile Cys Ser Asn Asn Pro Thr Cys Trp Ala Ile Ser Lys
            35                  40                  45

CGT ATC CCG                                                         153
Arg Ile Pro
    50
```

(2) INFORMATION FOR SEQ ID NO: 36:

(i) SEQUENCE CHARACTERISTICS:
        (A) LENGTH: 99 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..99

(xi) SEQUENCE DESCRIPTION: SEQ ID NO: 36:

| AAA | CCG | AAC | AAC | GAT | TTC | CAT | TTC | GAA | GTG | TTC | AAC | TTC | GTG | CCG | AGC | 48 |
| Lys | Pro | Asn | Asn | Asp | Phe | His | Phe | Glu | Val | Phe | Asn | Phe | Val | Pro | Ser | |
| 1 | | | | 5 | | | | | 10 | | | | | 15 | | |

| AGC | ATC | TGC | AGC | AAC | AAC | CCG | ACC | TGC | TGG | GCG | ATC | AGC | AAA | CGT | ATC | 96 |
| Ser | Ile | Cys | Ser | Asn | Asn | Pro | Thr | Cys | Trp | Ala | Ile | Ser | Lys | Arg | Ile | |
| | | | 20 | | | | | 25 | | | | | 30 | | | |

CCG                                                                                             99
Pro (2) INFORMATION FOR SEQ ID NO: 37:

(i) SEQUENCE CHARACTERISTICS:
        (A) LENGTH: 183 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..183

(xi) SEQUENCE DESCRIPTION: SEQ ID NO: 37:

| AGC | ACC | CAG | ACC | AAC | AAA | CCG | AGC | ACC | AAA | AGC | CGT | AGC | AAA | AAC | CCG | 48 |
| Ser | Thr | Gln | Thr | Asn | Lys | Pro | Ser | Thr | Lys | Ser | Arg | Ser | Lys | Asn | Pro | |
| 1 | | | | 5 | | | | | 10 | | | | | 15 | | |

| CCG | AAA | AAA | CCG | AAA | GAT | GAT | TAC | CAC | TTC | GAA | GTG | TTC | AAC | TTC | GTG | 96 |
| Pro | Lys | Lys | Pro | Lys | Asp | Asp | Tyr | His | Phe | Glu | Val | Phe | Asn | Phe | Val | |
| | | | 20 | | | | | 25 | | | | | 30 | | | |

| CCC | TGC | AGC | ATC | TGC | GGC | AAC | AAC | CAG | CTG | TGC | AAA | AGC | ATC | TGC | AAA | 144 |
| Pro | Cys | Ser | Ile | Cys | Gly | Asn | Asn | Gln | Leu | Cys | Lys | Ser | Ile | Cys | Lys | |
| | | 35 | | | | | 40 | | | | | 45 | | | | |

| ACC | ATC | CCG | AGC | AAC | AAA | CCG | AAA | AAG | AAA | CCG | ACC | ATC | 183 |
| Thr | Ile | Pro | Ser | Asn | Lys | Pro | Lys | Lys | Lys | Pro | Thr | Ile | |
| 50 | | | | | 55 | | | | | 60 | | | |

(2) INFORMATION FOR SEQ ID NO: 38:

(i) SEQUENCE CHARACTERISTICS:
        (A) LENGTH: 177 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..177

(xi) SEQUENCE DESCRIPTION: SEQ ID NO: 38:

| AGC | ACC | CAG | ACC | AAC | AAA | CCG | AGC | ACC | AAA | AGC | CGT | AGC | AAA | AAC | CCG | 48 |
| Ser | Thr | Gln | Thr | Asn | Lys | Pro | Ser | Thr | Lys | Ser | Arg | Ser | Lys | Asn | Pro | |
| 1 | | | | 5 | | | | | 10 | | | | | 15 | | |

| CCG | AAA | AAA | CCG | AAA | GAT | GAT | TAC | CAC | TTC | GAA | GTG | TTC | AAC | TTC | GTG | 96 |
| Pro | Lys | Lys | Pro | Lys | Asp | Asp | Tyr | His | Phe | Glu | Val | Phe | Asn | Phe | Val | |
| | | | 20 | | | | | 25 | | | | | 30 | | | |

| CCC | TGC | AGC | ATC | TGC | GGC | AAC | AAC | CAG | CTG | TGC | AAA | AGC | ATC | TGC | AAA | 144 |
| Pro | Cys | Ser | Ile | Cys | Gly | Asn | Asn | Gln | Leu | Cys | Lys | Ser | Ile | Cys | Lys | |
| | | 35 | | | | | 40 | | | | | 45 | | | | |

| ACC | ATC | CCG | AGC | AAC | AAA | CCG | AAA | AAG | AAA | CCG | 177 |
| Thr | Ile | Pro | Ser | Asn | Lys | Pro | Lys | Lys | Lys | Pro | |
| 50 | | | | | 55 | | | | | | |

(2) INFORMATION FOR SEQ ID NO: 39:

(i) SEQUENCE CHARACTERISTICS:
        (A) LENGTH: 171 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..171

(xi) SEQUENCE DESCRIPTION: SEQ ID NO: 39:

```
AGC ACC CAG ACC AAC AAA CCG AGC ACC AAA AGC CGT AGC AAA AAC CCG      48
Ser Thr Gln Thr Asn Lys Pro Ser Thr Lys Ser Arg Ser Lys Asn Pro
 1               5                  10                  15

CCG AAA AAA CCG AAA GAT GAT TAC CAC TTC GAA GTG TTC AAC TTC GTG      96
Pro Lys Lys Pro Lys Asp Asp Tyr His Phe Glu Val Phe Asn Phe Val
                20                  25                  30

CCC TGC AGC ATC TGC GGC AAC AAC CAG CTG TGC AAA AGC ATC TGC AAA     144
Pro Cys Ser Ile Cys Gly Asn Asn Gln Leu Cys Lys Ser Ile Cys Lys
            35                  40                  45

ACC ATC CCG AGC AAC AAA CCG AAA AAG                                 171
Thr Ile Pro Ser Asn Lys Pro Lys Lys
        50                  55
```

(2) INFORMATION FOR SEQ ID NO: 40:

(i) SEQUENCE CHARACTERISTICS:
        (A) LENGTH: 165 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..165

(xi) SEQUENCE DESCRIPTION: SEQ ID NO: 40:

```
AGC ACC CAG ACC AAC AAA CCG AGC ACC AAA AGC CGT AGC AAA AAC CCG      48
Ser Thr Gln Thr Asn Lys Pro Ser Thr Lys Ser Arg Ser Lys Asn Pro
 1               5                  10                  15

CCG AAA AAA CCG AAA GAT GAT TAC CAC TTC GAA GTG TTC AAC TTC GTG      96
Pro Lys Lys Pro Lys Asp Asp Tyr His Phe Glu Val Phe Asn Phe Val
                20                  25                  30

CCC TGC AGC ATC TGC GGC AAC AAC CAG CTG TGC AAA AGC ATC TGC AAA     144
Pro Cys Ser Ile Cys Gly Asn Asn Gln Leu Cys Lys Ser Ile Cys Lys
            35                  40                  45

ACC ATC CCG AGC AAC AAA CCG                                         165
Thr Ile Pro Ser Asn Lys Pro
        50                  55
```

(2) INFORMATION FOR SEQ ID NO: 41:

(i) SEQUENCE CHARACTERISTICS:
        (A) LENGTH: 159 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS (B) LOCATION:1..159

(xi) SEQUENCE DESCRIPTION: SEQ ID NO: 41:

| AGC | ACC | CAG | ACC | AAC | AAA | CCG | AGC | ACC | AAA | AGC | CGT | AGC | AAA | AAC | CCG | 48 |
|-----|-----|-----|-----|-----|-----|-----|-----|-----|-----|-----|-----|-----|-----|-----|-----|----|
| Ser | Thr | Gln | Thr | Asn | Lys | Pro | Ser | Thr | Lys | Ser | Arg | Ser | Lys | Asn | Pro |    |
| 1   |     |     |     | 5   |     |     |     |     | 10  |     |     |     |     | 15  |     |    |

| CCG | AAA | AAA | CCG | AAA | GAT | GAT | TAC | CAC | TTC | GAA | GTG | TTC | AAC | TTC | GTG | 96 |
| Pro | Lys | Lys | Pro | Lys | Asp | Asp | Tyr | His | Phe | Glu | Val | Phe | Asn | Phe | Val |    |
|     |     | 20  |     |     |     |     | 25  |     |     |     |     | 30  |     |     |     |    |

| CCC | TGC | AGC | ATC | TGC | GGC | AAC | AAC | CAG | CTG | TGC | AAA | AGC | ATC | TGC | AAA | 144 |
| Pro | Cys | Ser | Ile | Cys | Gly | Asn | Asn | Gln | Leu | Cys | Lys | Ser | Ile | Cys | Lys |     |
|     |     | 35  |     |     |     |     | 40  |     |     |     |     | 45  |     |     |     |     |

ACC ATC CCG AGC AAC                                                                 159
Thr Ile Pro Ser Asn
    50

(2) INFORMATION FOR SEQ ID NO: 42:

(i) SEQUENCE CHARACTERISTICS:
        (A) LENGTH: 153 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..153

(xi) SEQUENCE DESCRIPTION: SEQ ID NO: 42:

| AGC | ACC | CAG | ACC | AAC | AAA | CCG | AGC | ACC | AAA | AGC | CGT | AGC | AAA | AAC | CCG | 48 |
| Ser | Thr | Gln | Thr | Asn | Lys | Pro | Ser | Thr | Lys | Ser | Arg | Ser | Lys | Asn | Pro |    |
| 1   |     |     |     | 5   |     |     |     |     | 10  |     |     |     |     | 15  |     |    |

| CCG | AAA | AAA | CCG | AAA | GAT | GAT | TAC | CAC | TTC | GAA | GTG | TTC | AAC | TTC | GTG | 96 |
| Pro | Lys | Lys | Pro | Lys | Asp | Asp | Tyr | His | Phe | Glu | Val | Phe | Asn | Phe | Val |    |
|     |     | 20  |     |     |     |     | 25  |     |     |     |     | 30  |     |     |     |    |

| CCC | TGC | AGC | ATC | TGC | GGC | AAC | AAC | CAG | CTG | TGC | AAA | AGC | ATC | TGC | AAA | 144 |
| Pro | Cys | Ser | Ile | Cys | Gly | Asn | Asn | Gln | Leu | Cys | Lys | Ser | Ile | Cys | Lys |     |
|     |     | 35  |     |     |     |     | 40  |     |     |     |     | 45  |     |     |     |     |

ACC ATC CCG                                                                         153
Thr Ile Pro
    50

(2) INFORMATION FOR SEQ ID NO: 43:

(i) SEQUENCE CHARACTERISTICS:
        (A) LENGTH: 99 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..99

(xi) SEQUENCE DESCRIPTION: SEQ ID NO: 43:

| AAA | CCG | AAA | GAT | GAT | TAC | CAC | TTC | GAA | GTG | TTC | AAC | TTC | GTG | CCC | TGC | 48 |
| Lys | Pro | Lys | Asp | Asp | Tyr | His | Phe | Glu | Val | Phe | Asn | Phe | Val | Pro | Cys |    |
| 1   |     |     |     | 5   |     |     |     |     | 10  |     |     |     |     | 15  |     |    |

| AGC | ATC | TGC | GGC | AAC | AAC | CAG | CTG | TGC | AAA | AGC | ATC | TGC | AAA | ACC | ATC | 96 |
| Ser | Ile | Cys | Gly | Asn | Asn | Gln | Leu | Cys | Lys | Ser | Ile | Cys | Lys | Thr | Ile |    |
|     |     | 20  |     |     |     |     | 25  |     |     |     |     | 30  |     |     |     |    |

CCG                                                                                  99

Pro (2) INFORMATION FOR SEQ ID NO: 44:

(i) SEQUENCE CHARACTERISTICS:
        (A) LENGTH: 183 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..183

(xi) SEQUENCE DESCRIPTION: SEQ ID NO: 44:

```
AGC ACC CAG ACC AAC AAA CCG AGC ACC AAA AGC CGT AGC AAA AAC CCG       48
Ser Thr Gln Thr Asn Lys Pro Ser Thr Lys Ser Arg Ser Lys Asn Pro
 1               5                  10                  15

CCG AAA AAA CCG AAA GAT GAT TAC CAC TTC GAA GTG TTC AAC TTC GTG       96
Pro Lys Lys Pro Lys Asp Asp Tyr His Phe Glu Val Phe Asn Phe Val
            20                  25                  30

CCC AGC AGC ATC TGC GGC AAC AAC CAG CTG TGC AAA AGC ATC AGC AAA      144
Pro Ser Ser Ile Cys Gly Asn Asn Gln Leu Cys Lys Ser Ile Ser Lys
        35                  40                  45

ACC ATC CCG AGC AAC AAA CCG AAA AAG AAA CCG ACC ATC                  183
Thr Ile Pro Ser Asn Lys Pro Lys Lys Lys Pro Thr Ile
    50                  55                  60
```

(2) INFORMATION FOR SEQ ID NO: 45:

(i) SEQUENCE CHARACTERISTICS:
        (A) LENGTH: 177 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..177

(xi) SEQUENCE DESCRIPTION: SEQ ID NO: 45:

```
AGC ACC CAG ACC AAC AAA CCG AGC ACC AAA AGC CGT AGC AAA AAC CCG       48
Ser Thr Gln Thr Asn Lys Pro Ser Thr Lys Ser Arg Ser Lys Asn Pro
 1               5                  10                  15

CCG AAA AAA CCG AAA GAT GAT TAC CAC TTC GAA GTG TTC AAC TTC GTG       96
Pro Lys Lys Pro Lys Asp Asp Tyr His Phe Glu Val Phe Asn Phe Val
            20                  25                  30

CCC AGC AGC ATC TGC GGC AAC AAC CAG CTG TGC AAA AGC ATC AGC AAA      144
Pro Ser Ser Ile Cys Gly Asn Asn Gln Leu Cys Lys Ser Ile Ser Lys
        35                  40                  45

ACC ATC CCG AGC AAC AAA CCG AAA AAG AAA CCG                          177
Thr Ile Pro Ser Asn Lys Pro Lys Lys Lys Pro
    50                  55
```

(2) INFORMATION FOR SEQ ID NO: 46:

(i) SEQUENCE CHARACTERISTICS:
        (A) LENGTH: 171 base pairs
        (B) TYPE: nucleotide
        (C) STRANDEDNESS: single
        (D) TOPOLOGY: linear (ii) MOLECULE TYPE: cDNA -continued

```
        (ix) FEATURE:
              (A) NAME/KEY: CDS
              (B) LOCATION:1..171

(xi) SEQUENCE DESCRIPTION: SEQ ID NO: 46:

AGC ACC CAG ACC AAC AAA CCG AGC ACC AAA AGC CGT AGC AAA AAC CCG      48
Ser Thr Gln Thr Asn Lys Pro Ser Thr Lys Ser Arg Ser Lys Asn Pro
 1               5                  10                  15

CCG AAA AAA CCG AAA GAT GAT TAC CAC TTC GAA GTG TTC AAC TTC GTG      96
Pro Lys Lys Pro Lys Asp Asp Tyr His Phe Glu Val Phe Asn Phe Val
             20                  25                  30

CCC AGC AGC ATC TGC GGC AAC AAC CAG CTG TGC AAA AGC ATC AGC AAA     144
Pro Ser Ser Ile Cys Gly Asn Asn Gln Leu Cys Lys Ser Ile Ser Lys
         35                  40                  45

ACC ATC CCG AGC AAC AAA CCG AAA AAG                                 171
Thr Ile Pro Ser Asn Lys Pro Lys Lys
         50                  55

(2) INFORMATION FOR SEQ ID NO: 47:

(i) SEQUENCE CHARACTERISTICS:
              (A) LENGTH: 165 base pairs
              (B) TYPE: nucleotide
              (C) STRANDEDNESS: single
              (D) TOPOLOGY: linear (ii) MOLECULE TYPE:  cDNA (ix) FEATURE:
              (A) NAME/KEY: CDS
              (B) LOCATION:1..165

(xi) SEQUENCE DESCRIPTION: SEQ ID NO: 47:

AGC ACC CAG ACC AAC AAA CCG AGC ACC AAA AGC CGT AGC AAA AAC CCG      48
Ser Thr Gln Thr Asn Lys Pro Ser Thr Lys Ser Arg Ser Lys Asn Pro
 1               5                  10                  15

CCG AAA AAA CCG AAA GAT GAT TAC CAC TTC GAA GTG TTC AAC TTC GTG      96
Pro Lys Lys Pro Lys Asp Asp Tyr His Phe Glu Val Phe Asn Phe Val
             20                  25                  30

CCC AGC AGC ATC TGC GGC AAC AAC CAG CTG TGC AAA AGC ATC AGC AAA     144
Pro Ser Ser Ile Cys Gly Asn Asn Gln Leu Cys Lys Ser Ile Ser Lys
         35                  40                  45

ACC ATC CCG AGC AAC AAA CCG                                         165
Thr Ile Pro Ser Asn Lys Pro
         50                  55

(2) INFORMATION FOR SEQ ID NO: 48:

(i) SEQUENCE CHARACTERISTICS:
              (A) LENGTH: 159 base pairs
              (B) TYPE: nucleotide
              (C) STRANDEDNESS: single
              (D) TOPOLOGY: linear (ii) MOLECULE TYPE:  cDNA (ix) FEATURE:
              (A) NAME/KEY: CDS
              (B) LOCATION:1..159

(xi) SEQUENCE DESCRIPTION: SEQ ID NO: 48:

AGC ACC CAG ACC AAC AAA CCG AGC ACC AAA AGC CGT AGC AAA AAC CCG      48
Ser Thr Gln Thr Asn Lys Pro Ser Thr Lys Ser Arg Ser Lys Asn Pro
 1               5                  10                  15

CCG AAA AAA CCG AAA GAT GAT TAC CAC TTC GAA GTG TTC AAC TTC GTG      96
Pro Lys Lys Pro Lys Asp Asp Tyr His Phe Glu Val Phe Asn Phe Val
             20                  25                  30
```

```
CCC AGC AGC ATC TGC GGC AAC AAC CAG CTG TGC AAA AGC ATC AGC AAA      144
Pro Ser Ser Ile Cys Gly Asn Asn Gln Leu Cys Lys Ser Ile Ser Lys
         35                  40                  45

ACC ATC CCG AGC AAC                                                  159
Thr Ile Pro Ser Asn
 50
```

(2) INFORMATION FOR SEQ ID NO: 49:

(i) SEQUENCE CHARACTERISTICS:
        (A) LENGTH: 153 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..153

(xi) SEQUENCE DESCRIPTION: SEQ ID NO: 49:

```
AGC ACC CAG ACC AAC AAA CCG AGC ACC AAA AGC CGT AGC AAA AAC CCG       48
Ser Thr Gln Thr Asn Lys Pro Ser Thr Lys Ser Arg Ser Lys Asn Pro
 1               5                  10                  15

CCG AAA AAA CCG AAA GAT GAT TAC CAC TTC GAA GTG TTC AAC TTC GTG       96
Pro Lys Lys Pro Lys Asp Asp Tyr His Phe Glu Val Phe Asn Phe Val
             20                  25                  30

CCC AGC AGC ATC TGC GGC AAC AAC CAG CTG TGC AAA AGC ATC AGC AAA      144
Pro Ser Ser Ile Cys Gly Asn Asn Gln Leu Cys Lys Ser Ile Ser Lys
         35                  40                  45

ACC ATC CCG                                                          153
Thr Ile Pro
 50
```

(2) INFORMATION FOR SEQ ID NO: 50:

(i) SEQUENCE CHARACTERISTICS:
        (A) LENGTH: 99 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..99

(xi) SEQUENCE DESCRIPTION: SEQ ID NO: 50:

```
AAA CCG AAA GAT GAT TAC CAC TTC GAA GTG TTC AAC TTC GTG CCC AGC       48
Lys Pro Lys Asp Asp Tyr His Phe Glu Val Phe Asn Phe Val Pro Ser
 1               5                  10                  15

AGC ATC TGC GGC AAC AAC CAG CTG TGC AAA AGC ATC AGC AAA ACC ATC       96
Ser Ile Cys Gly Asn Asn Gln Leu Cys Lys Ser Ile Ser Lys Thr Ile
             20                  25                  30

CCG                                                                   99
Pro
```

(2) INFORMATION FOR SEQ ID NO: 51:

(i) SEQUENCE CHARACTERISTICS:
        (A) LENGTH: 303 base pairs
        (B) TYPE: nucleotide
        (C) STRANDEDNESS: single
        (D) TOPOLOGY: linear (ii) MOLECULE TYPE: cDNA (ix) FEATURE:
    (A) NAME/KEY: CDS
    (B) LOCATION:1..303

(xi) SEQUENCE DESCRIPTION: SEQ ID NO: 51:

```
CAA AAC AGA AAA ATC AAA GGT CAA TCA ACA CTA CCA GCC ACA AGA AAA    48
Gln Asn Arg Lys Ile Lys Gly Gln Ser Thr Leu Pro Ala Thr Arg Lys
 1               5                  10                  15

CCA CCA ATT AAT CCA TCA GGA AGC ATC CCA CCA GAA AAC CAT CAA GAC    96
Pro Pro Ile Asn Pro Ser Gly Ser Ile Pro Pro Glu Asn His Gln Asp
             20                  25                  30

CAC AAC AAC TTC CAA ACA CTC CCC TAT GTT CCC TGC AGT ACA TGT GAA   144
His Asn Asn Phe Gln Thr Leu Pro Tyr Val Pro Cys Ser Thr Cys Glu
         35                  40                  45

GGT AAT CTT GCA TGC TTA TCA CTC TGC CAT ATT GAG ACG GAA AGA GCA   192
Gly Asn Leu Ala Cys Leu Ser Leu Cys His Ile Glu Thr Glu Arg Ala
     50                  55                  60

CCA AGC AGA GCA CCA ACA ATC ACC CTC AAA AAG ACA CCA AAA CCA AAA   240
Pro Ser Arg Ala Pro Thr Ile Thr Leu Lys Lys Thr Pro Lys Pro Lys
 65                  70                  75                  80

ACC ACA AAA AAG CCA ACC AAG ACA ACA ATC CAT CAC AGA ACC AGC CCA   288
Thr Thr Lys Lys Pro Thr Lys Thr Thr Ile His His Arg Thr Ser Pro
                 85                  90                  95

GAA ACC AAA CTG CAA                                               303
Glu Thr Lys Leu Gln
            100
```

(2) INFORMATION FOR SEQ ID NO: 52:

(i) SEQUENCE CHARACTERISTICS:
        (A) LENGTH: 303 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..303

(xi) SEQUENCE DESCRIPTION: SEQ ID NO: 52:

```
CAA AAC AGA AAA ATC AAA GGT CAA TCA ACA CTA CCA GCC ACA AGA AAA    48
Gln Asn Arg Lys Ile Lys Gly Gln Ser Thr Leu Pro Ala Thr Arg Lys
 1               5                  10                  15

CCA CCA ATT AAT CCA TCA GGA AGC ATC CCA CCA GAA AAC CAT CAA GAC    96
Pro Pro Ile Asn Pro Ser Gly Ser Ile Pro Pro Glu Asn His Gln Asp
             20                  25                  30

CAC AAC AAC TTC CAA ACA CTC CCC TAT GTT CCC AGC AGT ACA TGT GAA   144
His Asn Asn Phe Gln Thr Leu Pro Tyr Val Pro Ser Ser Thr Cys Glu
         35                  40                  45

GGT AAT CTT GCA TGC TTA TCA CTC AGC CAT ATT GAG ACG GAA AGA GCA   192
Gly Asn Leu Ala Cys Leu Ser Leu Ser His Ile Glu Thr Glu Arg Ala
     50                  55                  60

CCA AGC AGA GCA CCA ACA ATC ACC CTC AAA AAG ACA CCA AAA CCA AAA   240
Pro Ser Arg Ala Pro Thr Ile Thr Leu Lys Lys Thr Pro Lys Pro Lys
 65                  70                  75                  80

ACC ACA AAA AAG CCA ACC AAG ACA ACA ATC CAT CAC AGA ACC AGC CCA   288
Thr Thr Lys Lys Pro Thr Lys Thr Thr Ile His His Arg Thr Ser Pro
                 85                  90                  95

GAA ACC AAA CTG CAA                                               303
Glu Thr Lys Leu Gln
```

100

(2) INFORMATION FOR SEQ ID NO: 53:

(i) SEQUENCE CHARACTERISTICS:
        (A) LENGTH: 183 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..183

(xi) SEQUENCE DESCRIPTION: SEQ ID NO: 53:

```
CTA CCA GCC ACA AGA AAA CCA CCA ATT AAT CCA TCA GGA AGC ATC CCA      48
Leu Pro Ala Thr Arg Lys Pro Pro Ile Asn Pro Ser Gly Ser Ile Pro
 1               5                  10                  15

CCA GAA AAC CAT CAA GAC CAC AAC AAC TTC CAA ACA CTC CCC TAT GTT      96
Pro Glu Asn His Gln Asp His Asn Asn Phe Gln Thr Leu Pro Tyr Val
             20                  25                  30

CCC TGC AGT ACA TGT GAA GGT AAT CTT GCA TGC TTA TCA CTC TGC CAT     144
Pro Cys Ser Thr Cys Glu Gly Asn Leu Ala Cys Leu Ser Leu Cys His
         35                  40                  45

ATT GAG ACG GAA AGA GCA CCA AGC AGA GCA CCA ACA ATC                 183
Ile Glu Thr Glu Arg Ala Pro Ser Arg Ala Pro Thr Ile
 50                  55                  60
```

(2) INFORMATION FOR SEQ ID NO: 54:

(i) SEQUENCE CHARACTERISTICS:
        (A) LENGTH: 177 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..177

(xi) SEQUENCE DESCRIPTION: SEQ ID NO: 54:

```
CTA CCA GCC ACA AGA AAA CCA CCA ATT AAT CCA TCA GGA AGC ATC CCA      48
Leu Pro Ala Thr Arg Lys Pro Pro Ile Asn Pro Ser Gly Ser Ile Pro
 1               5                  10                  15

CCA GAA AAC CAT CAA GAC CAC AAC AAC TTC CAA ACA CTC CCC TAT GTT      96
Pro Glu Asn His Gln Asp His Asn Asn Phe Gln Thr Leu Pro Tyr Val
             20                  25                  30

CCC TGC AGT ACA TGT GAA GGT AAT CTT GCA TGC TTA TCA CTC TGC CAT     144
Pro Cys Ser Thr Cys Glu Gly Asn Leu Ala Cys Leu Ser Leu Cys His
         35                  40                  45

ATT GAG ACG GAA AGA GCA CCA AGC AGA GCA CCA                         177
Ile Glu Thr Glu Arg Ala Pro Ser Arg Ala Pro
 50                  55
```

(2) INFORMATION FOR SEQ ID NO: 55:

(i) SEQUENCE CHARACTERISTICS:
        (A) LENGTH: 171 base pairs
        (B) TYPE: nucleotide
        (C) STRANDEDNESS: single
        (D) TOPOLOGY: linear (ii) MOLECULE TYPE: cDNA

```
    (ix) FEATURE:
         (A) NAME/KEY: CDS
         (B) LOCATION:1..171

(xi) SEQUENCE DESCRIPTION: SEQ ID NO: 55:

CTA CCA GCC ACA AGA AAA CCA CCA ATT AAT CCA TCA GGA AGC ATC CCA        48
Leu Pro Ala Thr Arg Lys Pro Pro Ile Asn Pro Ser Gly Ser Ile Pro
 1               5                  10                  15

CCA GAA AAC CAT CAA GAC CAC AAC AAC TTC CAA ACA CTC CCC TAT GTT        96
Pro Glu Asn His Gln Asp His Asn Asn Phe Gln Thr Leu Pro Tyr Val
                20                  25                  30

CCC TGC AGT ACA TGT GAA GGT AAT CTT GCA TGC TTA TCA CTC TGC CAT       144
Pro Cys Ser Thr Cys Glu Gly Asn Leu Ala Cys Leu Ser Leu Cys His
            35                  40                  45

ATT GAG ACG GAA AGA GCA CCA AGC AGA                                   171
Ile Glu Thr Glu Arg Ala Pro Ser Arg
        50                  55

(2) INFORMATION FOR SEQ ID NO: 56:

(i) SEQUENCE CHARACTERISTICS:
        (A) LENGTH: 165 base pairs
        (B) TYPE: nucleotide
        (C) STRANDEDNESS: single
        (D) TOPOLOGY: linear (ii) MOLECULE TYPE:  cDNA (ix) FEATURE:
         (A) NAME/KEY: CDS
         (B) LOCATION:1..165

(xi) SEQUENCE DESCRIPTION: SEQ ID NO: 56:

CTA CCA GCC ACA AGA AAA CCA CCA ATT AAT CCA TCA GGA AGC ATC CCA        48
Leu Pro Ala Thr Arg Lys Pro Pro Ile Asn Pro Ser Gly Ser Ile Pro
 1               5                  10                  15

CCA GAA AAC CAT CAA GAC CAC AAC AAC TTC CAA ACA CTC CCC TAT GTT        96
Pro Glu Asn His Gln Asp His Asn Asn Phe Gln Thr Leu Pro Tyr Val
                20                  25                  30

CCC TGC AGT ACA TGT GAA GGT AAT CTT GCA TGC TTA TCA CTC TGC CAT       144
Pro Cys Ser Thr Cys Glu Gly Asn Leu Ala Cys Leu Ser Leu Cys His
            35                  40                  45

ATT GAG ACG GAA AGA GCA CCA                                           165
Ile Glu Thr Glu Arg Ala Pro
        50                  55

(2) INFORMATION FOR SEQ ID NO: 57:

(i) SEQUENCE CHARACTERISTICS:
        (A) LENGTH: 159 base pairs
        (B) TYPE: nucleotide
        (C) STRANDEDNESS: single
        (D) TOPOLOGY: linear (ii) MOLECULE TYPE:  cDNA (ix) FEATURE:
         (A) NAME/KEY: CDS
         (B) LOCATION:1..159

(xi) SEQUENCE DESCRIPTION: SEQ ID NO: 57:

CTA CCA GCC ACA AGA AAA CCA CCA ATT AAT CCA TCA GGA AGC ATC CCA        48
Leu Pro Ala Thr Arg Lys Pro Pro Ile Asn Pro Ser Gly Ser Ile Pro
 1               5                  10                  15

CCA GAA AAC CAT CAA GAC CAC AAC AAC TTC CAA ACA CTC CCC TAT GTT        96
Pro Glu Asn His Gln Asp His Asn Asn Phe Gln Thr Leu Pro Tyr Val
                20                  25                  30
```

```
CCC TGC AGT ACA TGT GAA GGT AAT CTT GCA TGC TTA TCA CTC TGC CAT      144
Pro Cys Ser Thr Cys Glu Gly Asn Leu Ala Cys Leu Ser Leu Cys His
        35                  40                  45

ATT GAG ACG GAA AGA                                                  159
Ile Glu Thr Glu Arg
    50
```

(2) INFORMATION FOR SEQ ID NO: 58:

(i) SEQUENCE CHARACTERISTICS:
        (A) LENGTH: 153 base pairs
        (B) TYPE: nucleotide
        (C) STRANDEDNESS: single
        (D) TOPOLOGY: linear (ii) MOLECULE TYPE:  cDNA (ix) FEATURE:
        (A) NAME/KEY: CDS
        (B) LOCATION:1..153

(xi) SEQUENCE DESCRIPTION: SEQ ID NO: 58:

```
CTA CCA GCC ACA AGA AAA CCA CCA ATT AAT CCA TCA GGA AGC ATC CCA       48
Leu Pro Ala Thr Arg Lys Pro Pro Ile Asn Pro Ser Gly Ser Ile Pro
 1               5                  10                  15

CCA GAA AAC CAT CAA GAC CAC AAC AAC TTC CAA ACA CTC CCC TAT GTT       96
Pro Glu Asn His Gln Asp His Asn Asn Phe Gln Thr Leu Pro Tyr Val
            20                  25                  30

CCC TGC AGT ACA TGT GAA GGT AAT CTT GCA TGC TTA TCA CTC TGC CAT      144
Pro Cys Ser Thr Cys Glu Gly Asn Leu Ala Cys Leu Ser Leu Cys His
        35                  40                  45

ATT GAG ACG                                                          153
Ile Glu Thr
    50
```

(2) INFORMATION FOR SEQ ID NO: 59:

(i) SEQUENCE CHARACTERISTICS:
        (A) LENGTH: 99 base pairs
        (B) TYPE: nucleotide
        (C) STRANDEDNESS: single
        (D) TOPOLOGY: linear (ii) MOLECULE TYPE:  cDNA (ix) FEATURE:
        (A) NAME/KEY: CDS
        (B) LOCATION:1..99

(xi) SEQUENCE DESCRIPTION: SEQ ID NO: 59:

```
AAC CAT CAA GAC CAC AAC AAC TTC CAA ACA CTC CCC TAT GTT CCC TGC       48
Asn His Gln Asp His Asn Asn Phe Gln Thr Leu Pro Tyr Val Pro Cys
 1               5                  10                  15

AGT ACA TGT GAA GGT AAT CTT GCA TGC TTA TCA CTC TGC CAT ATT GAG       96
Ser Thr Cys Glu Gly Asn Leu Ala Cys Leu Ser Leu Cys His Ile Glu
            20                  25                  30

ACG                                                                   99
Thr
```

(2) INFORMATION FOR SEQ ID NO: 60:

(i) SEQUENCE CHARACTERISTICS:
        (A) LENGTH: 183 base pairs
        (B) TYPE: nucleotide
        (C) STRANDEDNESS: single
        (D) TOPOLOGY: linear

```
    (ii) MOLECULE TYPE:  cDNA (ix) FEATURE:
         (A) NAME/KEY: CDS
         (B) LOCATION:1..183

(xi) SEQUENCE DESCRIPTION: SEQ ID NO: 60:

CTA CCA GCC ACA AGA AAA CCA CCA ATT AAT CCA TCA GGA AGC ATC CCA          48
Leu Pro Ala Thr Arg Lys Pro Pro Ile Asn Pro Ser Gly Ser Ile Pro
 1               5                  10                  15

CCA GAA AAC CAT CAA GAC CAC AAC AAC TTC CAA ACA CTC CCC TAT GTT          96
Pro Glu Asn His Gln Asp His Asn Asn Phe Gln Thr Leu Pro Tyr Val
                20                  25                  30

CCC AGC AGT ACA TGT GAA GGT AAT CTT GCA TGC TTA TCA CTC AGC CAT         144
Pro Ser Ser Thr Cys Glu Gly Asn Leu Ala Cys Leu Ser Leu Ser His
             35                  40                  45

ATT GAG ACG GAA AGA GCA CCA AGC AGA GCA CCA ACA ATC                     183
Ile Glu Thr Glu Arg Ala Pro Ser Arg Ala Pro Thr Ile
             50                  55                  60

(2) INFORMATION FOR SEQ ID NO: 61:

(i) SEQUENCE CHARACTERISTICS:
         (A) LENGTH: 177 base pairs
         (B) TYPE: nucleotide
         (C) STRANDEDNESS: single
         (D) TOPOLOGY: linear (ii) MOLECULE TYPE:  cDNA (ix) FEATURE:
         (A) NAME/KEY: CDS
         (B) LOCATION:1..177

(xi) SEQUENCE DESCRIPTION: SEQ ID NO: 61:

CTA CCA GCC ACA AGA AAA CCA CCA ATT AAT CCA TCA GGA AGC ATC CCA          48
Leu Pro Ala Thr Arg Lys Pro Pro Ile Asn Pro Ser Gly Ser Ile Pro
 1               5                  10                  15

CCA GAA AAC CAT CAA GAC CAC AAC AAC TTC CAA ACA CTC CCC TAT GTT          96
Pro Glu Asn His Gln Asp His Asn Asn Phe Gln Thr Leu Pro Tyr Val
                20                  25                  30

CCC AGC AGT ACA TGT GAA GGT AAT CTT GCA TGC TTA TCA CTC AGC CAT         144
Pro Ser Ser Thr Cys Glu Gly Asn Leu Ala Cys Leu Ser Leu Ser His
             35                  40                  45

ATT GAG ACG GAA AGA GCA CCA AGC AGA GCA CCA                             177
Ile Glu Thr Glu Arg Ala Pro Ser Arg Ala Pro
             50                  55

(2) INFORMATION FOR SEQ ID NO: 62:

(i) SEQUENCE CHARACTERISTICS:
         (A) LENGTH: 171 base pairs
         (B) TYPE: nucleotide
         (C) STRANDEDNESS: single
         (D) TOPOLOGY: linear (ii) MOLECULE TYPE:  cDNA (ix) FEATURE:
         (A) NAME/KEY: CDS
         (B) LOCATION:1..171

(xi) SEQUENCE DESCRIPTION: SEQ ID NO: 62:

CTA CCA GCC ACA AGA AAA CCA CCA ATT AAT CCA TCA GGA AGC ATC CCA          48
Leu Pro Ala Thr Arg Lys Pro Pro Ile Asn Pro Ser Gly Ser Ile Pro
 1               5                  10                  15

CCA GAA AAC CAT CAA GAC CAC AAC AAC TTC CAA ACA CTC CCC TAT GTT          96
```

```
Pro Glu Asn His Gln Asp His Asn Asn Phe Gln Thr Leu Pro Tyr Val
             20                  25                  30

CCC AGC AGT ACA TGT GAA GGT AAT CTT GCA TGC TTA TCA CTC AGC CAT        144
Pro Ser Ser Thr Cys Glu Gly Asn Leu Ala Cys Leu Ser Leu Ser His
         35                  40                  45

ATT GAG ACG GAA AGA GCA CCA AGC AGA                                    171
Ile Glu Thr Glu Arg Ala Pro Ser Arg
     50                  55

(2) INFORMATION FOR SEQ ID NO: 63:

(i) SEQUENCE CHARACTERISTICS:
         (A) LENGTH: 165 base pairs
         (B) TYPE: nucleotide
         (C) STRANDEDNESS: single
         (D) TOPOLOGY: linear (ii) MOLECULE TYPE: cDNA (ix) FEATURE:
         (A) NAME/KEY: CDS
         (B) LOCATION:1..165

(xi) SEQUENCE DESCRIPTION: SEQ ID NO: 63:

CTA CCA GCC ACA AGA AAA CCA CCA ATT AAT CCA TCA GGA AGC ATC CCA         48
Leu Pro Ala Thr Arg Lys Pro Pro Ile Asn Pro Ser Gly Ser Ile Pro
 1               5                  10                  15

CCA GAA AAC CAT CAA GAC CAC AAC AAC TTC CAA ACA CTC CCC TAT GTT         96
Pro Glu Asn His Gln Asp His Asn Asn Phe Gln Thr Leu Pro Tyr Val
             20                  25                  30

CCC AGC AGT ACA TGT GAA GGT AAT CTT GCA TGC TTA TCA CTC AGC CAT        144
Pro Ser Ser Thr Cys Glu Gly Asn Leu Ala Cys Leu Ser Leu Ser His
         35                  40                  45

ATT GAG ACG GAA AGA GCA CCA                                            165
Ile Glu Thr Glu Arg Ala Pro
     50                  55

(2) INFORMATION FOR SEQ ID NO: 64:

(i) SEQUENCE CHARACTERISTICS:
         (A) LENGTH: 159 base pairs
         (B) TYPE: nucleotide
         (C) STRANDEDNESS: single
         (D) TOPOLOGY: linear (ii) MOLECULE TYPE: cDNA (ix) FEATURE:
         (A) NAME/KEY: CDS
         (B) LOCATION:1..159

(xi) SEQUENCE DESCRIPTION: SEQ ID NO: 64:

CTA CCA GCC ACA AGA AAA CCA CCA ATT AAT CCA TCA GGA AGC ATC CCA         48
Leu Pro Ala Thr Arg Lys Pro Pro Ile Asn Pro Ser Gly Ser Ile Pro
 1               5                  10                  15

CCA GAA AAC CAT CAA GAC CAC AAC AAC TTC CAA ACA CTC CCC TAT GTT         96
Pro Glu Asn His Gln Asp His Asn Asn Phe Gln Thr Leu Pro Tyr Val
             20                  25                  30

CCC AGC AGT ACA TGT GAA GGT AAT CTT GCA TGC TTA TCA CTC AGC CAT        144
Pro Ser Ser Thr Cys Glu Gly Asn Leu Ala Cys Leu Ser Leu Ser His
         35                  40                  45

ATT GAG ACG GAA AGA                                                    159
Ile Glu Thr Glu Arg
     50

(2) INFORMATION FOR SEQ ID NO: 65:
```

(i) SEQUENCE CHARACTERISTICS:
    (A) LENGTH: 153 base pairs
    (B) TYPE: nucleotide
    (C) STRANDEDNESS: single
    (D) TOPOLOGY: linear (ii) MOLECULE TYPE: cDNA (ix) FEATURE:
    (A) NAME/KEY: CDS
    (B) LOCATION:1..153

(xi) SEQUENCE DESCRIPTION: SEQ ID NO: 65:

```
CTA CCA GCC ACA AGA AAA CCA CCA ATT AAT CCA TCA GGA AGC ATC CCA    48
Leu Pro Ala Thr Arg Lys Pro Pro Ile Asn Pro Ser Gly Ser Ile Pro
 1               5                  10                  15

CCA GAA AAC CAT CAA GAC CAC AAC AAC TTC CAA ACA CTC CCC TAT GTT    96
Pro Glu Asn His Gln Asp His Asn Asn Phe Gln Thr Leu Pro Tyr Val
                20                  25                  30

CCC AGC AGT ACA TGT GAA GGT AAT CTT GCA TGC TTA TCA CTC AGC CAT   144
Pro Ser Ser Thr Cys Glu Gly Asn Leu Ala Cys Leu Ser Leu Ser His
            35                  40                  45

ATT GAG ACG                                                       153
Ile Glu Thr
    50
```

(2) INFORMATION FOR SEQ ID NO: 66:

(i) SEQUENCE CHARACTERISTICS:
    (A) LENGTH: 99 base pairs
    (B) TYPE: nucleotide
    (C) STRANDEDNESS: single
    (D) TOPOLOGY: linear (ii) MOLECULE TYPE: cDNA (ix) FEATURE:
    (A) NAME/KEY: CDS
    (B) LOCATION:1..99

(xi) SEQUENCE DESCRIPTION: SEQ ID NO: 66:

```
AAC CAT CAA GAC CAC AAC AAC TTC CAA ACA CTC CCC TAT GTT CCC AGC    48
Asn His Gln Asp His Asn Asn Phe Gln Thr Leu Pro Tyr Val Pro Ser
 1               5                  10                  15

AGT ACA TGT GAA GGT AAT CTT GCA TGC TTA TCA CTC AGC CAT ATT GAG    96
Ser Thr Cys Glu Gly Asn Leu Ala Cys Leu Ser Leu Ser His Ile Glu
                20                  25                  30

ACG                                                                99
Thr
```

(2) INFORMATION FOR SEQ ID NO: 67:

(i) SEQUENCE CHARACTERISTICS:
    (A) LENGTH: 51 base pairs
    (B) TYPE: nucleotide
    (C) STRANDEDNESS: single
    (D) TOPOLOGY: linear (ii) MOLECULE TYPE: cDNA (ix) FEATURE:
    (A) NAME/KEY: CDS
    (B) LOCATION:1..51

(xi) SEQUENCE DESCRIPTION: SEQ ID NO: 67:

```
GTT CCC TGC AGT ACA TGT GAA GGT AAT CTT GCA TGC TTA TCA CTC TGC    48
Val Pro Cys Ser Thr Cys Glu Gly Asn Leu Ala Cys Leu Ser Leu Cys
 1               5                  10                  15
```

```
CAT                                                                    51
His
```

(2) INFORMATION FOR SEQ ID NO: 68:

(i) SEQUENCE CHARACTERISTICS:
        (A) LENGTH: 51 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..51

(xi) SEQUENCE DESCRIPTION: SEQ ID NO: 68:

```
GTT CCC AGC AGT ACA TGT GAA GGT AAT CTT GCA TGC TTA TCA CTC AGC        48
Val Pro Ser Ser Thr Cys Glu Gly Asn Leu Ala Cys Leu Ser Leu Ser
 1               5                  10                  15

CAT                                                                    51
His
```

(2) INFORMATION FOR SEQ ID NO: 69:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: Peptide (ix) FEATURE:
        (A) NAME/KEY: Modified-site
        (B) LOCATION:12
        (D) OTHER INFORMATION:/Xaa means Orn (ix) FEATURE:
        (A) NAME/KEY: Modified-site
        (B) LOCATION:16
        (D) OTHER INFORMATION:/Xaa means Orn (xi) SEQUENCE DESCRIPTION: SEQ ID NO: 69:

```
Val Pro Asp Ser Thr Asp Glu Gly Asn Leu Ala Xaa Leu Ser Leu Xaa
 1               5                  10                  15

His
```

(2) INFORMATION FOR SEQ ID NO: 70:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: Peptide (ix) FEATURE:
        (A) NAME/KEY: Modified-site
        (B) LOCATION:12
        (D) OTHER INFORMATION:/Xaa means Orn (xi) SEQUENCE DESCRIPTION: SEQ ID NO: 70:

```
Val Pro Ser Ser Thr Asp Glu Gly Asn Leu Ala Xaa Leu Ser Leu Ser
 1               5                  10                  15

His
```

(2) INFORMATION FOR SEQ ID NO: 71:

(i) SEQUENCE CHARACTERISTICS:
        (A) LENGTH: 42 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..42

(xi) SEQUENCE DESCRIPTION: SEQ ID NO: 71:

```
AGT ACA TGT GAA GGT AAT CTT GCA TGC TTA TCA CTC TGC CAT        42
Ser Thr Cys Glu Gly Asn Leu Ala Cys Leu Ser Leu Cys His
 1               5                  10
```

(2) INFORMATION FOR SEQ ID NO: 72:

(i) SEQUENCE CHARACTERISTICS:
        (A) LENGTH: 42 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..42

(xi) SEQUENCE DESCRIPTION: SEQ ID NO: 72:

```
AGT ACA TGT GAA GGT AAT CTT GCA TGC TTA TCA CTC AGC CAT        42
Ser Thr Cys Glu Gly Asn Leu Ala Cys Leu Ser Leu Ser His
 1               5                  10
```

(2) INFORMATION FOR SEQ ID NO: 73:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: Peptide (ix) FEATURE:
        (A) NAME/KEY: Modified-site
        (B) LOCATION:9
        (D) OTHER INFORMATION:/Xaa means Orn (xi) SEQUENCE DESCRIPTION: SEQ ID NO: 73:

```
Ser Thr Asp Glu Gly Asn Leu Ala Xaa Leu Ser Leu Ser His
 1               5                  10
```

(2) INFORMATION FOR SEQ ID NO: 74:

(i) SEQUENCE CHARACTERISTICS:
        (A) LENGTH: 657 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..657

(xi) SEQUENCE DESCRIPTION: SEQ ID NO: 74:

-continued

| | |
|---|---|
| AAA TAT GGA GTA AGT GAC TAT TAC AAG AAT CTA ATC AAC AAT GCC AAA<br>Lys Tyr Gly Val Ser Asp Tyr Tyr Lys Asn Leu Ile Asn Asn Ala Lys<br>1               5                   10                  15 | 48 |
| ACT GTT GAA GGC GTA AAA GAC CTT CAA GCA CAA GTT GTT GAA TCA GCG<br>Thr Val Glu Gly Val Lys Asp Leu Gln Ala Gln Val Val Glu Ser Ala<br>        20                  25                  30 | 96 |
| AAG AAA GCG CGT ATT TCA GAA GCA ACA GAT GGC TTA TCT GAT TTC TTG<br>Lys Lys Ala Arg Ile Ser Glu Ala Thr Asp Gly Leu Ser Asp Phe Leu<br>    35                  40                  45 | 144 |
| AAA TCA CAA ACA CCT GCT GAA GAT ACT GTT AAA TCA ATT GAA TTA GCT<br>Lys Ser Gln Thr Pro Ala Glu Asp Thr Val Lys Ser Ile Glu Leu Ala<br>50                  55                  60 | 192 |
| GAA GCT AAA GTC TTA GCT AAC AGA GAA CTT GAC AAA TAT GGA GTA AGT<br>Glu Ala Lys Val Leu Ala Asn Arg Glu Leu Asp Lys Tyr Gly Val Ser<br>65                  70                  75                  80 | 240 |
| GAC TAT CAC AAG AAC CTA ATC AAC AAT GCC AAA ACT GTT GAA GGT GTA<br>Asp Tyr His Lys Asn Leu Ile Asn Asn Ala Lys Thr Val Glu Gly Val<br>            85                  90                  95 | 288 |
| AAA GAC CTT CAA GCA CAA GTT GTT GAA TCA GCG AAG AAA GCG CGT ATT<br>Lys Asp Leu Gln Ala Gln Val Val Glu Ser Ala Lys Lys Ala Arg Ile<br>        100                 105                 110 | 336 |
| TCA GAA GCA ACA GAT GGC TTA TCT GAT TTC TTG AAA TCA CAA ACA CCT<br>Ser Glu Ala Thr Asp Gly Leu Ser Asp Phe Leu Lys Ser Gln Thr Pro<br>    115                 120                 125 | 384 |
| GCT GAA GAT ACT GTT AAA TCA ATT GAA TTA GCT GAA GCT AAA GTC TTA<br>Ala Glu Asp Thr Val Lys Ser Ile Glu Leu Ala Glu Ala Lys Val Leu<br>130                 135                 140 | 432 |
| GCT AAC AGA GAA CTT GAC AAA TAT GGA GTA AGT GAC TAT TAC AAG AAC<br>Ala Asn Arg Glu Leu Asp Lys Tyr Gly Val Ser Asp Tyr Tyr Lys Asn<br>145                 150                 155                 160 | 480 |
| CTA ATC AAC AAT GCC AAA ACT GTT GAA GGT GTA AAA GCA CTG ATA GAT<br>Leu Ile Asn Asn Ala Lys Thr Val Glu Gly Val Lys Ala Leu Ile Asp<br>            165                 170                 175 | 528 |
| GAA ATT TTA GCT GCA TTA CCT AAG ACT GAC ACT TAC AAA TTA ATC CTT<br>Glu Ile Leu Ala Ala Leu Pro Lys Thr Asp Thr Tyr Lys Leu Ile Leu<br>        180                 185                 190 | 576 |
| AAT GGT AAA ACA TTG AAA GGC GAA ACA ACT ACT GAA GCT GTT GAT GCT<br>Asn Gly Lys Thr Leu Lys Gly Glu Thr Thr Thr Glu Ala Val Asp Ala<br>    195                 200                 205 | 624 |
| GCT ACT GCA AGA TCT TTC AAT TTC CCT ATC CTC<br>Ala Thr Ala Arg Ser Phe Asn Phe Pro Ile Leu<br>210                 215 | 657 |

(2) INFORMATION FOR SEQ ID NO: 75:

(i) SEQUENCE CHARACTERISTICS:
        (A) LENGTH: 324 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..324

(xi) SEQUENCE DESCRIPTION: SEQ ID NO: 75:

| | |
|---|---|
| AAA TAT GGA GTA AGT GAC TAT CAC AAG AAC CTA ATC AAC AAT GCC AAA<br>Lys Tyr Gly Val Ser Asp Tyr His Lys Asn Leu Ile Asn Asn Ala Lys<br>1               5                   10                  15 | 48 |
| ACT GTT GAA GGT GTA AAA GAC CTT CAA GCA CAA GTT GTT GAA TCA GCG | 96 |

```
Thr Val Glu Gly Val Lys Asp Leu Gln Ala Gln Val Val Glu Ser Ala
             20                  25                  30

AAG AAA GCG CGT ATT TCA GAA GCA ACA GAT GGC TTA TCT GAT TTC TTG      144
Lys Lys Ala Arg Ile Ser Glu Ala Thr Asp Gly Leu Ser Asp Phe Leu
         35                  40                  45

AAA TCA CAA ACA CCT GCT GAA GAT ACT GTT AAA TCA ATT GAA TTA GCT      192
Lys Ser Gln Thr Pro Ala Glu Asp Thr Val Lys Ser Ile Glu Leu Ala
 50                  55                  60

GAA GCT AAA GTC TTA GCT AAC AGA GAA CTT GAC AAA TAT GGA GTA AGT      240
Glu Ala Lys Val Leu Ala Asn Arg Glu Leu Asp Lys Tyr Gly Val Ser
 65                  70                  75                  80

GAC TAT TAC AAG AAC CTA ATC AAC AAT GCC AAA ACT GTT GAA GGT GTA      288
Asp Tyr Tyr Lys Asn Leu Ile Asn Asn Ala Lys Thr Val Glu Gly Val
             85                  90                  95

AAA GCA CTG ATA GAT GAA ATT TTA GCT GCA TTA CCT                       324
Lys Ala Leu Ile Asp Glu Ile Leu Ala Ala Leu Pro
            100                 105

(2) INFORMATION FOR SEQ ID NO: 76:

(i) SEQUENCE CHARACTERISTICS:
        (A) LENGTH: 1050 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..1050

(xi) SEQUENCE DESCRIPTION: SEQ ID NO: 76:

ATG AAA GCA ATT TTC GTA CTG AAT GCG CAA CAC GAT GAA GCC GTA GAC       48
Met Lys Ala Ile Phe Val Leu Asn Ala Gln His Asp Glu Ala Val Asp
 1               5                  10                  15

GCG AAT TTC GAC CAA TTC AAC AAA TAT GGA GTA AGT GAC TAT TAC AAG       96
Ala Asn Phe Asp Gln Phe Asn Lys Tyr Gly Val Ser Asp Tyr Tyr Lys
             20                  25                  30

AAT CTA ATC AAC AAT GCC AAA ACT GTT GAA GGC GTA AAA GAC CTT CAA      144
Asn Leu Ile Asn Asn Ala Lys Thr Val Glu Gly Val Lys Asp Leu Gln
         35                  40                  45

GCA CAA GTT GTT GAA TCA GCG AAG AAA GCG CGT ATT TCA GAA GCA ACA      192
Ala Gln Val Val Glu Ser Ala Lys Lys Ala Arg Ile Ser Glu Ala Thr
 50                  55                  60

GAT GGC TTA TCT GAT TTC TTG AAA TCA CAA ACA CCT GCT GAA GAT ACT      240
Asp Gly Leu Ser Asp Phe Leu Lys Ser Gln Thr Pro Ala Glu Asp Thr
 65                  70                  75                  80

GTT AAA TCA ATT GAA TTA GCT GAA GCT AAA GTC TTA GCT AAC AGA GAA      288
Val Lys Ser Ile Glu Leu Ala Glu Ala Lys Val Leu Ala Asn Arg Glu
             85                  90                  95

CTT GAC AAA TAT GGA GTA AGT GAC TAT CAC AAG AAC CTA ATC AAC AAT      336
Leu Asp Lys Tyr Gly Val Ser Asp Tyr His Lys Asn Leu Ile Asn Asn
            100                 105                 110

GCC AAA ACT GTT GAA GGT GTA AAA GAC CTT CAA GCA CAA GTT GTT GAA      384
Ala Lys Thr Val Glu Gly Val Lys Asp Leu Gln Ala Gln Val Val Glu
            115                 120                 125

TCA GCG AAG AAA GCG CGT ATT TCA GAA GCA ACA GAT GGC TTA TCT GAT      432
Ser Ala Lys Lys Ala Arg Ile Ser Glu Ala Thr Asp Gly Leu Ser Asp
130                 135                 140

TTC TTG AAA TCA CAA ACA CCT GCT GAA GAT ACT GTT AAA TCA ATT GAA      480
Phe Leu Lys Ser Gln Thr Pro Ala Glu Asp Thr Val Lys Ser Ile Glu
145                 150                 155                 160
```

```
TTA GCT GAA GCT AAA GTC TTA GCT AAC AGA GAA CTT GAC AAA TAT GGA    528
Leu Ala Glu Ala Lys Val Leu Ala Asn Arg Glu Leu Asp Lys Tyr Gly
            165                 170                 175

GTA AGT GAC TAT TAC AAG AAC CTA ATC AAC AAT GCC AAA ACT GTT GAA    576
Val Ser Asp Tyr Tyr Lys Asn Leu Ile Asn Asn Ala Lys Thr Val Glu
            180                 185                 190

GGT GTA AAA GCA CTG ATA GAT GAA ATT TTA GCT GCA TTA CCT AAG ACT    624
Gly Val Lys Ala Leu Ile Asp Glu Ile Leu Ala Ala Leu Pro Lys Thr
            195                 200                 205

GAC ACT TAC AAA TTA ATC CTT AAT GGT AAA ACA TTG AAA GGC GAA ACA    672
Asp Thr Tyr Lys Leu Ile Leu Asn Gly Lys Thr Leu Lys Gly Glu Thr
    210                 215                 220

ACT ACT GAA GCT GTT GAT GCT GCT ACT GCA AGA TCT TTC AAT TTC CCT    720
Thr Thr Glu Ala Val Asp Ala Ala Thr Ala Arg Ser Phe Asn Phe Pro
225                 230                 235                 240

ATC CTC GAG AAT TCC ATG ACC GTG AAA ACC AAA AAC ACC ACG ACC ACC    768
Ile Leu Glu Asn Ser Met Thr Val Lys Thr Lys Asn Thr Thr Thr Thr
                245                 250                 255

CAG ACC CAG CCG AGC AAA CCG ACC ACC AAA CAG CGT CAG AAC AAA CCG    816
Gln Thr Gln Pro Ser Lys Pro Thr Thr Lys Gln Arg Gln Asn Lys Pro
            260                 265                 270

CCG AAC AAA CCG AAC AAC GAT TTC CAT TTC GAA GTG TTC AAC TTC GTG    864
Pro Asn Lys Pro Asn Asn Asp Phe His Phe Glu Val Phe Asn Phe Val
            275                 280                 285

CCG TGC AGC ATC TGC AGC AAC AAC CCG ACC TGC TGG GCG ATC TGC AAA    912
Pro Cys Ser Ile Cys Ser Asn Asn Pro Thr Cys Trp Ala Ile Cys Lys
            290                 295                 300

CGT ATC CCG AAC AAA AAA CCG GGC AAA AAA ACC ACG ACC AAA CCG ACC    960
Arg Ile Pro Asn Lys Lys Pro Gly Lys Lys Thr Thr Thr Lys Pro Thr
305                 310                 315                 320

AAA AAA CCG ACC TTC AAA ACC ACC AAA AAA GAT CAT AAA CCG CAG ACC   1008
Lys Lys Pro Thr Phe Lys Thr Thr Lys Lys Asp His Lys Pro Gln Thr
                325                 330                 335

ACC AAA CCG AAA GAA GTG CCG ACC ACC AAA CCG GTC GAC TAA           1050
Thr Lys Pro Lys Glu Val Pro Thr Thr Lys Pro Val Asp
            340                 345

(2) INFORMATION FOR SEQ ID NO: 77:

(i) SEQUENCE CHARACTERISTICS:
        (A) LENGTH: 1071 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..1071

(xi) SEQUENCE DESCRIPTION: SEQ ID NO: 77:

ATG AAA GCA ATT TTC GTA CTG AAT GCG CAA CAC GAT GAA GCC GTA GAC     48
Met Lys Ala Ile Phe Val Leu Asn Ala Gln His Asp Glu Ala Val Asp
1               5                   10                  15

GCG AAT TTC GAC CAA TTC AAC AAA TAT GGA GTA AGT GAC TAT TAC AAG     96
Ala Asn Phe Asp Gln Phe Asn Lys Tyr Gly Val Ser Asp Tyr Tyr Lys
            20                  25                  30

AAT CTA ATC AAC AAT GCC AAA ACT GTT GAA GGC GTA AAA GAC CTT CAA    144
Asn Leu Ile Asn Asn Ala Lys Thr Val Glu Gly Val Lys Asp Leu Gln
        35                  40                  45

GCA CAA GTT GTT GAA TCA GCG AAG AAA GCG CGT ATT TCA GAA GCA ACA    192
```

| | | | | | | | | | | | | | |
|---|---|---|---|---|---|---|---|---|---|---|---|---|---|
| Ala | Gln | Val | Val | Glu | Ser | Ala | Lys | Lys | Ala | Arg | Ile | Ser | Glu | Ala | Thr |
| | 50 | | | | 55 | | | | 60 | | | | |

```
GAT GGC TTA TCT GAT TTC TTG AAA TCA CAA ACA CCT GCT GAA GAT ACT       240
Asp Gly Leu Ser Asp Phe Leu Lys Ser Gln Thr Pro Ala Glu Asp Thr
 65              70                  75                  80

GTT AAA TCA ATT GAA TTA GCT GAA GCT AAA GTC TTA GCT AAC AGA GAA       288
Val Lys Ser Ile Glu Leu Ala Glu Ala Lys Val Leu Ala Asn Arg Glu
                 85                  90                  95

CTT GAC AAA TAT GGA GTA AGT GAC TAT CAC AAG AAC CTA ATC AAC AAT       336
Leu Asp Lys Tyr Gly Val Ser Asp Tyr His Lys Asn Leu Ile Asn Asn
            100                 105                 110

GCC AAA ACT GTT GAA GGT GTA AAA GAC CTT CAA GCA CAA GTT GTT GAA       384
Ala Lys Thr Val Glu Gly Val Lys Asp Leu Gln Ala Gln Val Val Glu
        115                 120                 125

TCA GCG AAG AAA GCG CGT ATT TCA GAA GCA ACA GAT GGC TTA TCT GAT       432
Ser Ala Lys Lys Ala Arg Ile Ser Glu Ala Thr Asp Gly Leu Ser Asp
    130                 135                 140

TTC TTG AAA TCA CAA ACA CCT GCT GAA GAT ACT GTT AAA TCA ATT GAA       480
Phe Leu Lys Ser Gln Thr Pro Ala Glu Asp Thr Val Lys Ser Ile Glu
145                 150                 155                 160

TTA GCT GAA GCT AAA GTC TTA GCT AAC AGA GAA CTT GAC AAA TAT GGA       528
Leu Ala Glu Ala Lys Val Leu Ala Asn Arg Glu Leu Asp Lys Tyr Gly
                165                 170                 175

GTA AGT GAC TAT TAC AAG AAC CTA ATC AAC AAT GCC AAA ACT GTT GAA       576
Val Ser Asp Tyr Tyr Lys Asn Leu Ile Asn Asn Ala Lys Thr Val Glu
            180                 185                 190

GGT GTA AAA GCA CTG ATA GAT GAA ATT TTA GCT GCA TTA CCT AAG ACT       624
Gly Val Lys Ala Leu Ile Asp Glu Ile Leu Ala Ala Leu Pro Lys Thr
        195                 200                 205

GAC ACT TAC AAA TTA ATC CTT AAT GGT AAA ACA TTG AAA GGC GAA ACA       672
Asp Thr Tyr Lys Leu Ile Leu Asn Gly Lys Thr Leu Lys Gly Glu Thr
    210                 215                 220

ACT ACT GAA GCT GTT GAT GCT GCT ACT GCA AGA TCT TTC AAT TTC CCT       720
Thr Thr Glu Ala Val Asp Ala Ala Thr Ala Arg Ser Phe Asn Phe Pro
225                 230                 235                 240

ATC CTC GAG AAT TCG AGC TCG GTA CCC GGG GAT CCT ATG ACC GTG AAA       768
Ile Leu Glu Asn Ser Ser Ser Val Pro Gly Asp Pro Met Thr Val Lys
                245                 250                 255

ACC AAA AAC ACC ACG ACC ACC CAG ACC CAG CCG AGC AAA CCG ACC ACC       816
Thr Lys Asn Thr Thr Thr Thr Gln Thr Gln Pro Ser Lys Pro Thr Thr
            260                 265                 270

AAA CAG CGT CAG AAC AAA CCG CCG AAC AAA CCG AAC AAC GAT TTC CAT       864
Lys Gln Arg Gln Asn Lys Pro Pro Asn Lys Pro Asn Asn Asp Phe His
        275                 280                 285

TTC GAA GTG TTC AAC TTC GTG CCG AGC AGC ATC TGC AGC AAC AAC CCG       912
Phe Glu Val Phe Asn Phe Val Pro Ser Ser Ile Cys Ser Asn Asn Pro
    290                 295                 300

ACC TGC TGG GCG ATC AGC AAA CGT ATC CCG AAC AAA AAA CCG GGC AAA       960
Thr Cys Trp Ala Ile Ser Lys Arg Ile Pro Asn Lys Lys Pro Gly Lys
305                 310                 315                 320

AAA ACC ACG ACC AAA CCG ACC AAA AAA CCG ACC TTC AAA ACC ACC AAA      1008
Lys Thr Thr Thr Lys Pro Thr Lys Lys Pro Thr Phe Lys Thr Thr Lys
                325                 330                 335

AAA GAT CAT AAA CCG CAG ACC ACC AAA CCG AAA GAA GTG CCG ACC ACC      1056
Lys Asp His Lys Pro Gln Thr Thr Lys Pro Lys Glu Val Pro Thr Thr
            340                 345                 350

AAA CCG GTC GAC TAA                                                  1071
Lys Pro Val Asp
        355
```

(2) INFORMATION FOR SEQ ID NO: 78:

(i) SEQUENCE CHARACTERISTICS:
        (A) LENGTH: 726 base pairs
        (B) TYPE: nucleotide
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..726

(xi) SEQUENCE DESCRIPTION: SEQ ID NO: 78:

```
ATG AAA GCA ATT TTC GTA CTG AAT GCG CAA CAC GAT GAA GCC GTA GAC        48
Met Lys Ala Ile Phe Val Leu Asn Ala Gln His Asp Glu Ala Val Asp
1               5                  10                  15

GCG AAT TTC GAC CAA TTC AAC AAA TAT GGA GTA AGT GAC TAT TAC AAG        96
Ala Asn Phe Asp Gln Phe Asn Lys Tyr Gly Val Ser Asp Tyr Tyr Lys
                20                  25                  30

AAT CTA ATC AAC AAT GCC AAA ACT GTT GAA GGC GTA AAA GAC CTT CAA       144
Asn Leu Ile Asn Asn Ala Lys Thr Val Glu Gly Val Lys Asp Leu Gln
            35                  40                  45

GCA CAA GTT GTT GAA TCA GCG AAG AAA GCG CGT ATT TCA GAA GCA ACA       192
Ala Gln Val Val Glu Ser Ala Lys Lys Ala Arg Ile Ser Glu Ala Thr
        50                  55                  60

GAT GGC TTA TCT GAT TTC TTG AAA TCA CAA ACA CCT GCT GAA GAT ACT       240
Asp Gly Leu Ser Asp Phe Leu Lys Ser Gln Thr Pro Ala Glu Asp Thr
65                  70                  75                  80

GTT AAA TCA ATT GAA TTA GCT GAA GCT AAA GTC TTA GCT AAC AGA GAA       288
Val Lys Ser Ile Glu Leu Ala Glu Ala Lys Val Leu Ala Asn Arg Glu
                85                  90                  95

CTT GAC AAA TAT GGA GTA AGT GAC TAT CAC AAG AAC CTA ATC AAC AAT       336
Leu Asp Lys Tyr Gly Val Ser Asp Tyr His Lys Asn Leu Ile Asn Asn
                100                 105                 110

GCC AAA ACT GTT GAA GGT GTA AAA GAC CTT CAA GCA CAA GTT GTT GAA       384
Ala Lys Thr Val Glu Gly Val Lys Asp Leu Gln Ala Gln Val Val Glu
            115                 120                 125

TCA GCG AAG AAA GCG CGT ATT TCA GAA GCA ACA GAT GGC TTA TCT GAT       432
Ser Ala Lys Lys Ala Arg Ile Ser Glu Ala Thr Asp Gly Leu Ser Asp
        130                 135                 140

TTC TTG AAA TCA CAA ACA CCT GCT GAA GAT ACT GTT AAA TCA ATT GAA       480
Phe Leu Lys Ser Gln Thr Pro Ala Glu Asp Thr Val Lys Ser Ile Glu
145                 150                 155                 160

TTA GCT GAA GCT AAA GTC TTA GCT AAC AGA GAA CTT GAC AAA TAT GGA       528
Leu Ala Glu Ala Lys Val Leu Ala Asn Arg Glu Leu Asp Lys Tyr Gly
                165                 170                 175

GTA AGT GAC TAT TAC AAG AAC CTA ATC AAC AAT GCC AAA ACT GTT GAA       576
Val Ser Asp Tyr Tyr Lys Asn Leu Ile Asn Asn Ala Lys Thr Val Glu
                180                 185                 190

GGT GTA AAA GCA CTG ATA GAT GAA ATT TTA GCT GCA TTA CCT AAG ACT       624
Gly Val Lys Ala Leu Ile Asp Glu Ile Leu Ala Ala Leu Pro Lys Thr
            195                 200                 205

GAC ACT TAC AAA TTA ATC CTT AAT GGT AAA ACA TTG AAA GGC GAA ACA       672
Asp Thr Tyr Lys Leu Ile Leu Asn Gly Lys Thr Leu Lys Gly Glu Thr
        210                 215                 220
```

-continued

```
ACT ACT GAA GCT GTT GAT GCT GCT ACT GCA AGA TCT TTC AAT TTC CCT        720
Thr Thr Glu Ala Val Asp Ala Ala Thr Ala Arg Ser Phe Asn Phe Pro
225             230             235             240

ATC CTC                                                                726
Ile Leu
```